United States Patent [19]
Ito et al.

[11] Patent Number: 6,117,071
[45] Date of Patent: Sep. 12, 2000

[54] ENDOSCOPE WITH MOVABLE IMAGING UNIT FOR ZOOMING OR FOCUSING

[75] Inventors: Keiji Ito; Ryuichi Hoshino; Shizuharu Miura, all of Saitama, Japan

[73] Assignee: Asahi Kogaku Kogyo Kabushiki Kaisha, Tokyo, Japan

[21] Appl. No.: 09/122,376

[22] Filed: Jul. 27, 1998

[30] Foreign Application Priority Data

| Jul. 29, 1997 | [JP] | Japan | 9-202677 |
| Jul. 29, 1997 | [JP] | Japan | 9-202678 |
| Aug. 6, 1997 | [JP] | Japan | 9-211587 |
| Aug. 6, 1997 | [JP] | Japan | 9-211588 |
| Aug. 6, 1997 | [JP] | Japan | 9-211589 |
| Aug. 7, 1997 | [JP] | Japan | 9-212894 |
| Aug. 7, 1997 | [JP] | Japan | 9-212895 |
| Aug. 7, 1997 | [JP] | Japan | 9-213030 |
| Jan. 16, 1998 | [JP] | Japan | 10-006222 |

[51] Int. Cl.[7] .................................................... A61B 1/05
[52] U.S. Cl. ........................ 600/168; 600/167; 600/129; 600/118
[58] Field of Search .................................. 600/167, 168, 600/173, 149, 150, 151, 129, 130, 117, 118, 103

[56] References Cited

U.S. PATENT DOCUMENTS

| 3,856,000 | 12/1974 | Chikama | 600/173 |
| 4,558,691 | 12/1985 | Okada . | |
| 4,765,313 | 8/1988 | Kumakura | 600/168 |
| 4,777,524 | 10/1988 | Nakajima et al. . | |
| 5,228,430 | 7/1993 | Sakamoto | 600/109 |
| 5,418,645 | 5/1995 | Coath et al. | 359/676 |
| 5,662,584 | 9/1997 | Hori et al. | 600/167 |

FOREIGN PATENT DOCUMENTS

| 63-21882 | 5/1988 | Japan . |
| 63-269113 | 11/1988 | Japan . |
| 5-12686 | 2/1993 | Japan . |

*Primary Examiner*—Joe Leubecker
*Attorney, Agent, or Firm*—Greenblum & Bernstein, P.L.C.

[57] ABSTRACT

An electronic endoscope includes a charge coupled device and provides macro-zooming function. The endoscope comprises an imaging unit including a plurality of optical elements forming an optical system and a support and guide mechanism for supporting and/or guiding the optical elements. The optical elements include a fixed lens, movable lenses, and a CCD. The support and guide mechanism comprises a casing including inner and outer cylinders. The axis of the inner cylinder defines a reference axis. A cam cylinder is fitted over the inner cylinder and is guided for rotational movement with no axial movement. An axial slider is fitted over the cam cylinder and guided for axial movement with no rotational movement. The axial slider is driven for axial movement through a manipulating lever provided on a handpiece. First and second carriages are fitted in the inner cylinder and guided for axial movement with no rotational movement. The fixed lens is secured to the casing, the movable lens are carried on the first carriage, and the CCD is carried on the second carriage. A first cam mechanism is provided to producing rotational movement of the cam cylinder in response to axial movement of the axial slider. A second cam mechanism is provided for producing respective axial movements of the carriages in response to rotational movement of the cam cylinder.

55 Claims, 17 Drawing Sheets

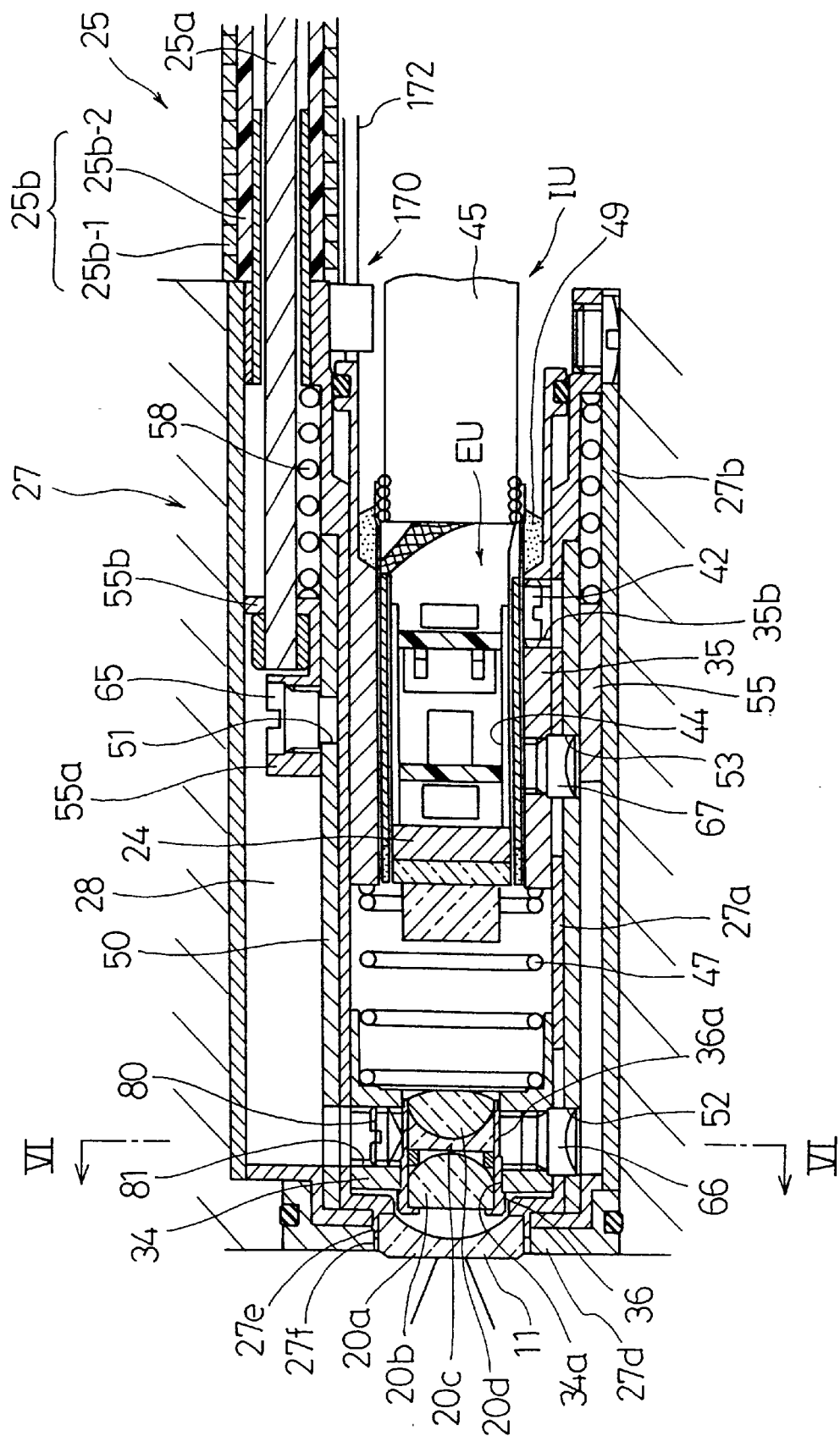

ENDOSCOPE WITH MOVABLE IMAGING UNIT FOR ZOOMING OR FOCUSING

The present disclosure relates to subject matters contained in Japanese Patent Application Nos. 9-202677 (filed on Jul. 29, 1997), 9-202678 (filed on Jul. 29, 1997), 9-211587 (filed on Aug. 6, 1997), 9-211588 (filed on Aug. 6, 1997), 9-211589 (filed on Aug. 6, 1997), 9-212894 (filed on Aug. 7, 1997), 9-212895 (filed on Aug. 7, 1997), 9-213030 (filed on Aug. 7, 1997) and 10-006222 (filed on Jan. 16, 1998), each of which is expressly incorporated herein by reference in its entirety.

BACKGROUND OF THE INVENTION

1. Field of the Invention

The present invention generally relates to an endoscope, and more particularly to an imaging unit used in an endoscope capable of providing focusing and/or zooming functions.

2. Description of the Related Art

There have been widely used various endoscopes for medical and other purposes to visualize the interior of a cavity, such as a hollow organ. One typical endoscope comprises a handpiece including a manipulating member mounted thereon, a tip unit including a generally cylindrical housing having front and rear ends, and an insertion tube extending between and interconnecting the handpiece and the tip unit, the insertion tube having a proximal end connected to the handpiece and a distal end connected to the rear end of the housing of the tip unit. When such endoscope is used for medical purposes, the tip unit and a part of the insertion tube are inserted into a human body. An imaging unit is housed in the housing of the tip unit for forming an image as viewed in a view field in front of the tip unit. A manipulation cable assembly is received in the insertion tube. The manipulation cable assembly has a proximal end operatively connected to the manipulating member on the handpiece and a distal end operatively connected to the imaging unit so as to allow a user to manipulate the imaging unit through the manipulating member on the handpiece. The imaging unit comprises a plurality of optical elements forming an optical system and a support and guide mechanism for supporting and/or guiding the plurality of optical elements.

One exemplified endoscope having the above construction is disclosed in Japanese published patent application No. Sho-63-269113 published on Nov. 7, 1998. According to this patent application, some of the lenses of the imaging unit are fixedly supported on the housing of the tip unit while the others are movable relative to the housing. The support and guide mechanism of the imaging unit comprises a movable carriage carrying the movable lenses thereon. The movable carriage is supported and guided for axial movement relative to the housing. The distal end of the manipulation cable assembly is operatively connected to the movable carriage. The movable carriage is driven through the manipulation cable assembly for axial movement relative to the housing in order to achieve focusing operation of the imaging unit.

Another tip unit of an endoscope having a similar imaging unit is disclosed in Japanese patent publication No. Hei-5-12686 published on Feb. 18, 1993. According to this patent publication, a movable carriage is driven through a manipulation cable assembly in order to achieve zooming operation of the imaging unit.

In either case, the pull and/or push forces required for driving the movable carriage will directly act on the movable carriage from the manipulation cable, while the movable carriage is supported and guided for axial movement by a certain support and guide mechanism which can not help suffering from allowances and clearances inevitably existing between movable components for smooth operation of the imaging unit. Such allowances and clearances often cause a minute but harmful tilt of the movable carriage, leading to partial blurring of the resultant image observed.

SUMMARY OF THE INVENTION

In view of the foregoing, it is an object of the present invention to provide an endoscope having an improved imaging unit in which a carriage may be driven by the manipulating cable for axial movement while producing substantially no tilt of the movable carriage, such that focusing and/or zooming operations of the imaging unit may be achieved without any partial blurring of the resultant image.

In accordance with one aspect the present invention, there is provided an endoscope comprising: a handpiece including a manipulating member mounted thereon; a tip unit having front and rear ends and including i) a housing and ii) an imaging unit housed in the housing for obtaining an image as viewed in a view field in front of the tip unit, the housing having front and rear ends; an insertion tube extending between and interconnecting the handpiece and the tip unit, the insertion tube having a proximal end connected to the handpiece and a distal end connected to the rear end of the housing of the tip unit; a manipulation cable assembly received in the insertion tube and having a proximal end operatively connected to the manipulating member and a distal end operatively connected to the imaging unit so as to allow a user to manipulate the imaging unit through the manipulating member.

The imaging unit comprises i) a plurality of optical elements forming an optical system and ii) a support and guide mechanism for supporting and/or guiding the plurality of optical elements. Further, the plurality of optical elements includes i) a device having an image-bearing surface on which an image is to be formed and ii) a plurality of lenses arranged in line along a common optical axis for forming an image on the image-bearing surface of the device.

The support and guide mechanism of the imaging unit comprises: i) a first member fixedly mounted in the housing and including a hollow cylindrical portion having an axis and front and rear ends, the axis of the hollow cylindrical portion being a reference axis and defining an axial direction; ii) a second member of a hollow cylindrical shape and having a cylindrical surface, the second member being fitted over the hollow cylindrical portion of the first member and being supported and guided for rotational movement about the reference axis with substantially no axial movement relative to the first member; iii) a third member supported and guided for axial movement relative to the first and second members with substantially no rotational movement about the reference axis, the third member being operatively connected to the distal end of the manipulation cable assembly; iv) at least one carriage carrying thereon one or more of the optical elements, the at least one carriage being supported and guided for axial movement relative to the first and second members with substantially no rotational movement about the reference axis; v) a first cam mechanism provided between the second and third members for producing rotational movement of the second member in response to axial movement of the third member; and vi) a second cam mechanism provided between the second member and the at least one carriage for producing axial movement of the at least one carriage in response to rotational movement of the second member.

The support and guide mechanism may preferably further comprise a first spring means for normally urging the third member in the axially forward direction.

The first cam mechanism may preferably comprise i) a first cam slot formed in the second member and extending obliquely with respect to generators of the cylindrical surface of the second member and ii) a first pin provided on the third member and engaging the first cam slot.

Further, in such case, it may be preferable that: the first cam slot has front and rear end edges; axially forward displacement of the third member is limited by the abutment of the first pin against the front end edge of the first cam slot; and axially rearward displacement of the third member is limited by the abutment of the first pin against the rear end edge of the first cam slot; whereby axially foremost and rearmost positions of the third member is defined by the geometry of the first cam slot.

Moreover, it may be preferable that: the first cam slot is helical in shape and extends such that the angle formed between a generator of the cylindrical surface of the second member and the first cam slot falls in a range from 10 to 45 degrees.

The plurality of lenses may include at least one movable lens; the at least one carriage may include a first carriage carrying thereon the at least one movable lens and a second carriage carrying thereon the device; the first cam mechanism may comprise i) a first cam slot formed in the second member and extending obliquely with respect to generators of the cylindrical surface of the second member and ii) a first pin provided on the third member and engaging the first cam slot; and the second cam mechanism may comprise i) second and third cam slots formed in the second member and extending obliquely with respect to generators of the cylindrical surface of the second member in opposite directions and ii) second and third pins provided on the first and second carriages, respectively, and engaging the second and third cam slots, respectively.

Further, in such case, it may be preferable that: the first cam slot has front and rear end edges and each of the second and third cam slots has first and second end edges; axially forward displacement of the third member is limited by the abutment of the first pin against the front end edge of the first cam slot, with a clearance remaining between the second pin and the first end edge of the second cam slot as well as a clearance remaining between the third pin and the first end edge of the third cam slot; and axially rearward displacement of the third member is limited by the abutment of the first pin against the rear end edge of the first cam slot, with a clearance remaining between the second pin and the second end edge of the second cam slot as well as a clearance remaining between the third pin and the second end edge of the third cam slot; whereby axially foremost and rearmost positions of the third member are defined by the geometry of the first cam slot.

Moreover, it may preferable that: the support and guide mechanism further comprises a first spring means for normally urging the third member in the axially forward direction; each of the second and third cam slots has side edges; and the support and guide mechanism further comprises a second spring means for normally urging the first and second carriages in the axially opposite directions apart from each other so as to keep the second and third pins in contact with one of the side edges of the second cam slot and one of the side edges of the third cam slot, respectively. In such case, the first and second spring means may preferably provide respective urging forces which are chosen such that i) a torque normally acting on and tending to rotate the second member in one direction is produced from the urging force of the second spring means through the second cam mechanism, ii) an axial force normally acting on and tending to move the third member in the axially rearward direction is produced from the torque through the first cam mechanism and iii) the urging force of the first spring means is greater than the axial force.

BRIEF DESCRIPTION OF THE DRAWINGS

The above and other objects, features and advantages of the present invention will be apparent from the following detailed description of a preferred embodiment thereof, reference being made to the accompanying drawings, in which:

FIGS. 5a and 5b are longitudinal sectional views of the imaging unit IU shown in FIG. 3, showing various components in their positions corresponding to the wide-end and zoom-up-end positions, respectively, of macro-zooming operation;

FIG. 7 is a cross-sectional view of the imaging unit IU taken along line VII—VII indicated in FIG. 5a;

DETAILED DESCRIPTION OF A PREFERRED EMBODIMENT

Figure 1:
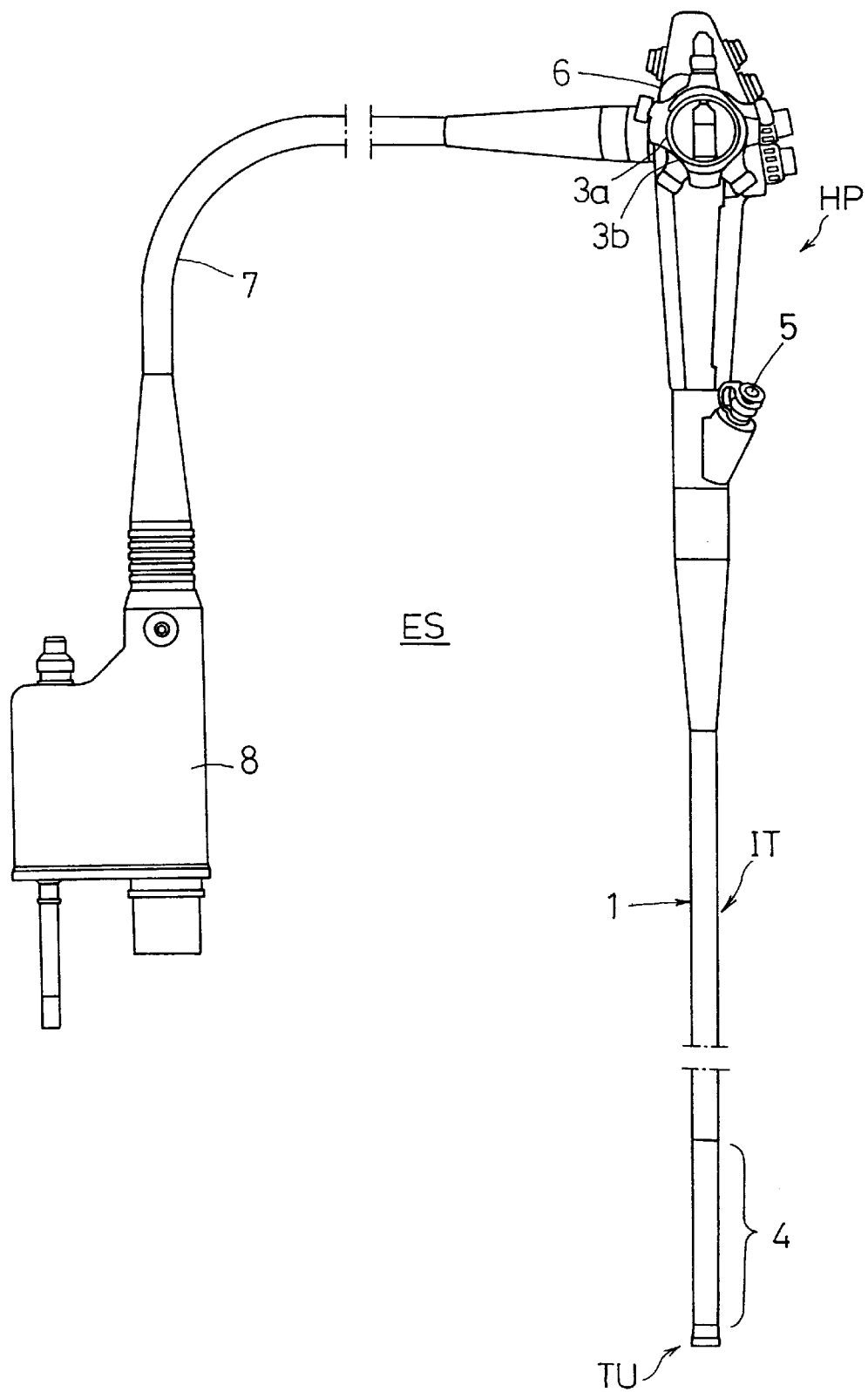
FIG. 1 shows an electronic endoscope ES according to a preferred embodiment of the present invention.

Referring to the accompanying drawings, a preferred embodiment of the present invention will be described in detail. Among different drawings like reference numerals are used to designate like elements, and repetitive description of the same elements are avoided for simplicity.

With reference to FIG. 1, there is shown an electronic endoscope ES in accordance with a preferred embodiment of the present invention. The endoscope ES comprises a handpiece HP, a tip unit TU, and an insertion tube IT extending between and interconnecting the handpiece HP and the tip unit TU. The tip unit TU includes a generally cylindrical housing 10 (FIGS. 5a and 5b) having front and rear ends. The housing 10 is made of a suitable plastic material. The insertion tube IT has a proximal end connected to the handpiece HP and a distal end connected to the rear end of the housing 10 of the tip unit TU. When the endoscope ES is used, the tip unit TU and a part of the insertion tube IT are inserted into a human body for endoscopic operations.

The tip unit TU includes an imaging unit IU (FIGS. 5a and 5b) housed in the housing 10 for obtaining an image as viewed in a view field in front of the tip unit TU, that is, for generating and transmitting video signals representing such an image. The insertion tube IT is sufficiently flexible and has an front end portion adjacent to the tip unit TU constructed as a steerable portion 4. The handpiece HP is adapted to be held by a user of the endoscope ES and has certain members manipulated by the user for endoscopic operations, including a pair of steering knobs 3a and 3b and an imaging unit manipulating lever 6. The pair of steering knobs 3a and 3b are operatively connected to the steerable portion 4. By manipulating the steering knobs 3a and 3b, the steerable porion 4 of the insertion tube IT may be curved into any desired direction with any desired curvature within a certain curvature range, so that the tip unit TU may be inserted with ease even into a relatively narrow and winding cavity. The imaging unit manipulating lever 6 is used to manipulate the imaging unit IU for macro-zooming operation, as described later in detail.

The insertion tube IT houses a plurality of inner tubes defining various channels, a set of steering cables 4f (FIG. 3), a shielded cable (electric cable) 45 (FIG. 3) for transmitting video signals, a manipulation cable assembly 25 (FIG. 3) for operating the imaging unit IU, and a pair of light-guides 18a and 18b (FIG. 4) each comprising a bundle of optical fibers, some of which are described below in more detail.

Among the inner tubes, a first inner tube defines a channel adapted to receive various endoscopic operation utensils, such as endoscopic forceps, laser-knives and others. The handpiece HP has a utensil mouth 5, which is provided at the front end of the handpiece HP and rising from the surface of the front end for introducing an endoscopic operation utensil into the channel.

The manipulation cable assembly 25 (FIGS. 5a, 5b and some other figures) received in the insertion tube IT has a proximal end operatively connected to the imaging unit manipulating lever 6 on the handpiece HP and a distal end operatively connected to the imaging unit IU so as to allow a user to manipulate the imaging unit IU through the manipulating lever 6. The manipulation cable assembly 25 comprises a length of flexible inner cable 25a made of twisted steel wires, and a corresponding length of flexible outer support tube 25b. The inner cable 25a is received in the outer support tube 25b for sliding movement in the longitudinal direction relative to the outer support tube 25b. The inner cable 25a is bendable but stiff against the tensile force. The outer support tube 25b is also bendable but stiff against the longitudinal compression force. The combination of an inner cable and an outer support tube of this kind is well known in the art. However, the outer support tube 25b used in the endoscope ES according to the present invention is considered novel, as described later in more detail.

The endoscope ES further comprises a connector unit 8 and an electrical/optical connection cord 7 extending between and interconnecting the handpiece HP and the connector unit 8. The connector unit 8 is adapted for detachable connection to a console 90 (FIG. 16) which includes a light source (not shown) and a video processor. The light source outputs illumination light which is transmitted through the connection cord 7 to the handpiece HP, and thence to the tip unit TU through the light-guides 18a and 18b housed in the insertion tube IT. The video processor in the console 90 serves to process the video signals received from the imaging unit IU in the endoscope ES and drive a display or video monitor in order to display the image as viewed in the view field in front of the tip unit TU. The console 90 will be describe later in more detail.

Figure 2:
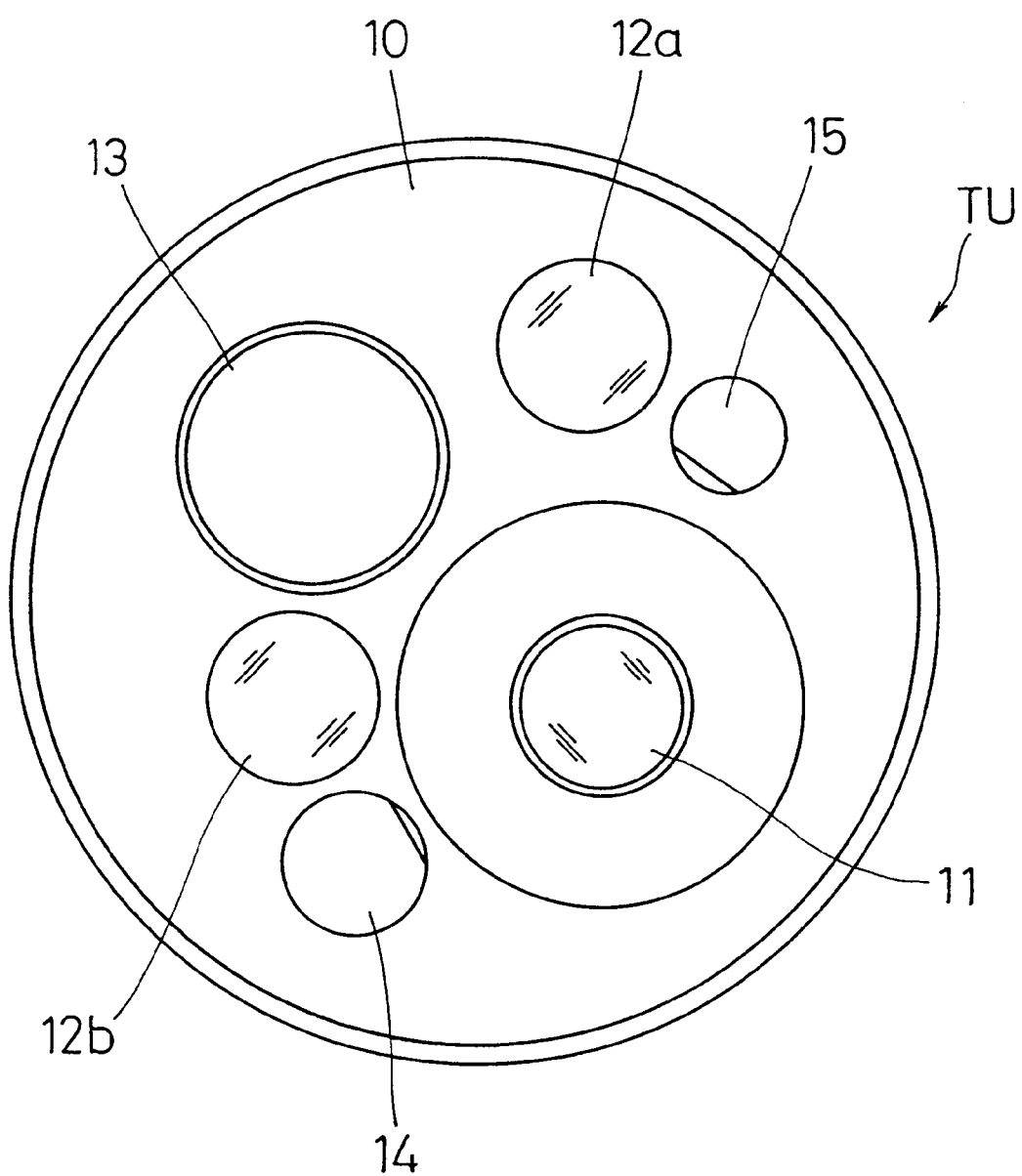
FIG. 2 is a front end view of the tip unit TU shown in FIG. 1.

FIG. 2 is a front end view of the tip unit TU. As shown, the tip unit TU has a view window 11 through which the view field in front of the tip unit TU may be observed from inside of the housing 10, a pair of illumination windows 12a and 12b through which illumination beams are projected to illuminate throughout the view field, an opening 13 through which the front end of an endoscopic operation utensil may project into the region in front of the tip unit TU, a $CO_2$-gas outlet 14 and an irrigation fluid outlet 15, all defined in the front end of the tip unit TU.

Figure 3:
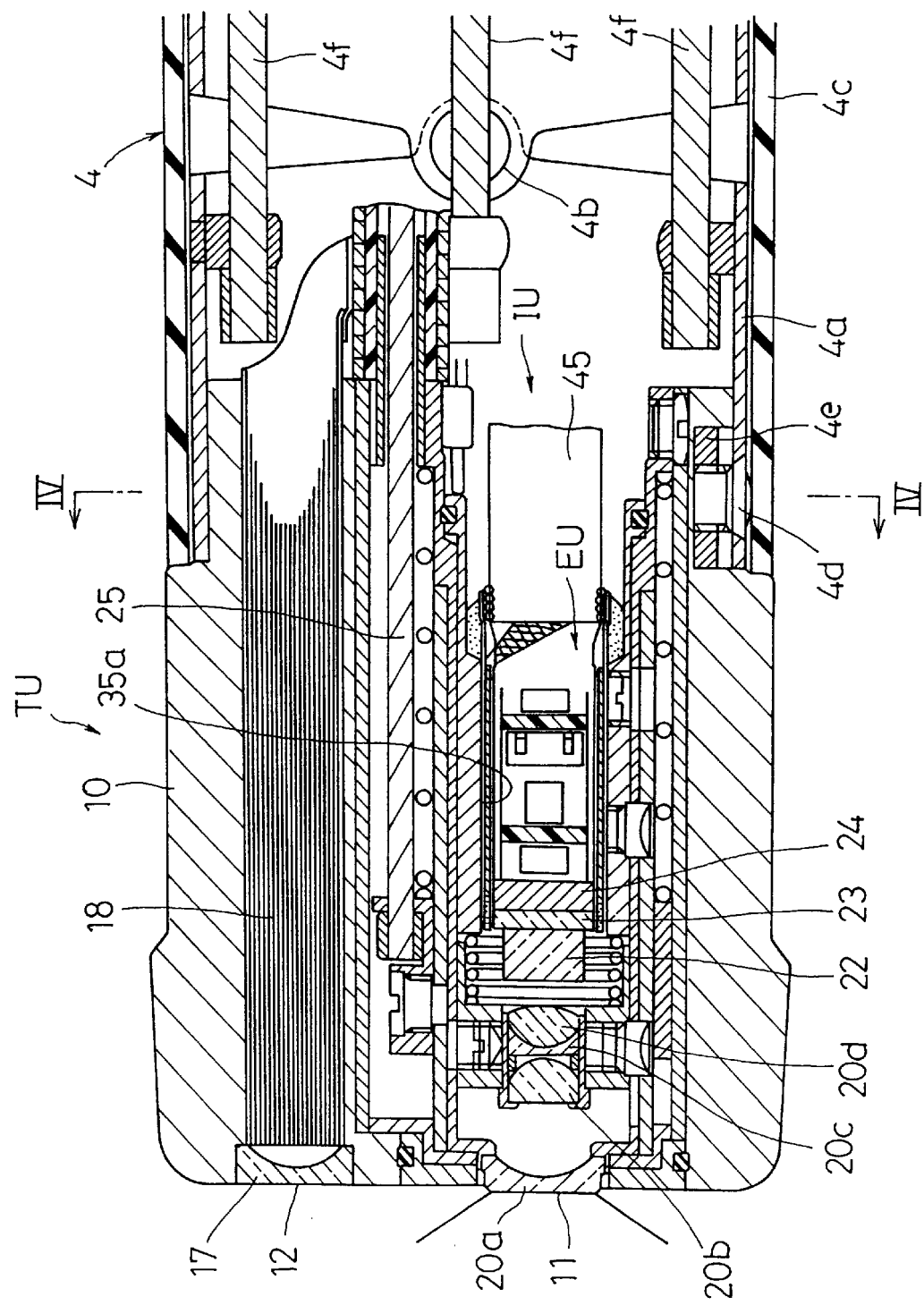
FIG. 3 is a longitudinal sectional view of the tip unit TU shown in FIGS. 1 and 2.
Figure 4:
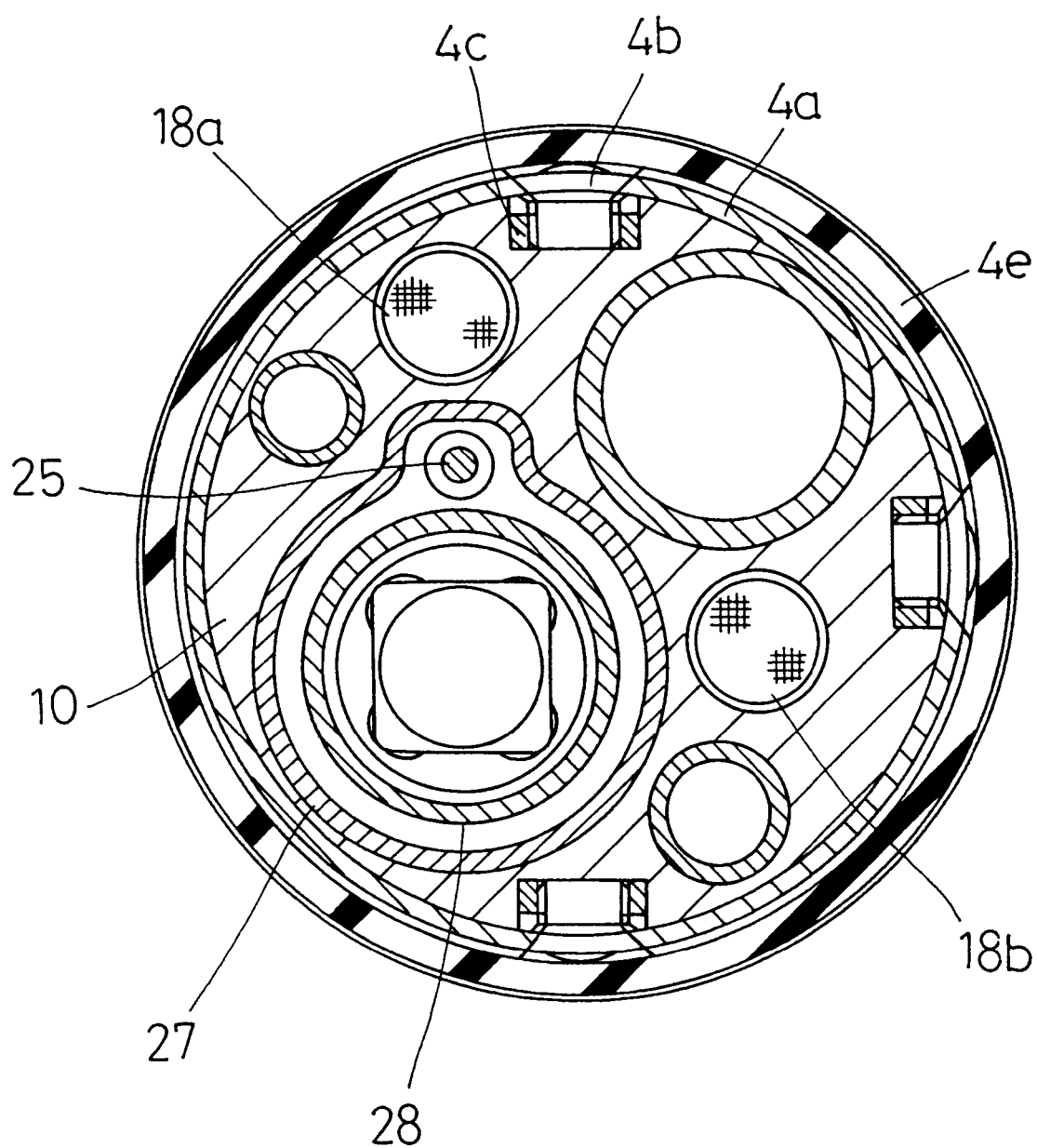
FIG. 4 is a cross-sectional view of the tip unit UT taken along the line IV—IV indicated in FIG. 3.

FIG. 3 is a longitudinal sectional view of the tip unit TU, showing the housing 10, the imaging unit IU, one of the light-guides 18a and the front end of the steerable portion 4 of the insertion tube IT. FIG. 4 is a cross-sectional view of the tip unit UT taken along line IV—IV indicated in FIG. 3.

As shown in FIGS. 3 and 4, each of the illumination windows (only one of them, 12a, is shown in FIG. 3) has a concave lens 17 tightly fitted therein, with the front end (or exit end) of the associated light-guide 18a or 18b (FIG. 4) being disposed adjacent and facing to the inner side of the concave lens 17. The concave lens 17 serves to diffuse the illumination light from the exit end of the light-guide 18 for illuminating throughout the view field. The imaging unit IU has a generally cylindrical shape, and the housing 10 has a cavity so shaped as to accommodate the imaging unit IU. The front end of the imaging unit IU is exposed to the outside of the housing 10 through a round opening 10a defined in the front end wall of the housing 10. The view window 11 is formed in the front end of the imaging unit IU.

The steerable portion 4 of the insertion tube IT, only the front end of which is shown in FIG. 3, comprises a plurality of rings 4a connected together or articulated by means of pairs of pins 4b into a chain of rings. Each pair of pins 4b provide pivotal connection between two adjacent rings 4a, allowing their relative rotation about an axis of each pair of pins 4b, which axis extends orthogonal to the longitudinal direction of the ring chain. Two pairs of pins adjacent to each other have their axes orthogonal to each other so that the ring chain is capable of curving in any directions with relatively small radii of curvature. The remaining portion of the insertion tube IT has a conventional structure capable of curving only with relatively large radii of curvature but less costly. The insertion tube IT includes an outer tube 4c made of a suitable, stretchable material such as a rubber, which defines the outer surface of the entire length of the insertion tube IT.

The foremost of the rings 4a of the steerable portion 4 is fitted over the rear end of the housing 10 and secured thereto by three set screws 4d. The housing 10 has three anchor pieces 4e fixedly received in respective recesses formed in the housing 10. Each anchor piece 4e has a threaded hole for threadable engagement with the corresponding set screw 4d. Four steering cables 4f (only three of them are shown in FIG. 3), which are received in the insertion tube IT as described above, are used to operatively interconnect the steering knobs 3a and 3b on the handpiece HP and the rings 4a of the steerable portion 4, such that the manipulation of the steering knobs 3a and 3b may cause the corresponding curving operation of the steerable portion 4.

Figure 5A:
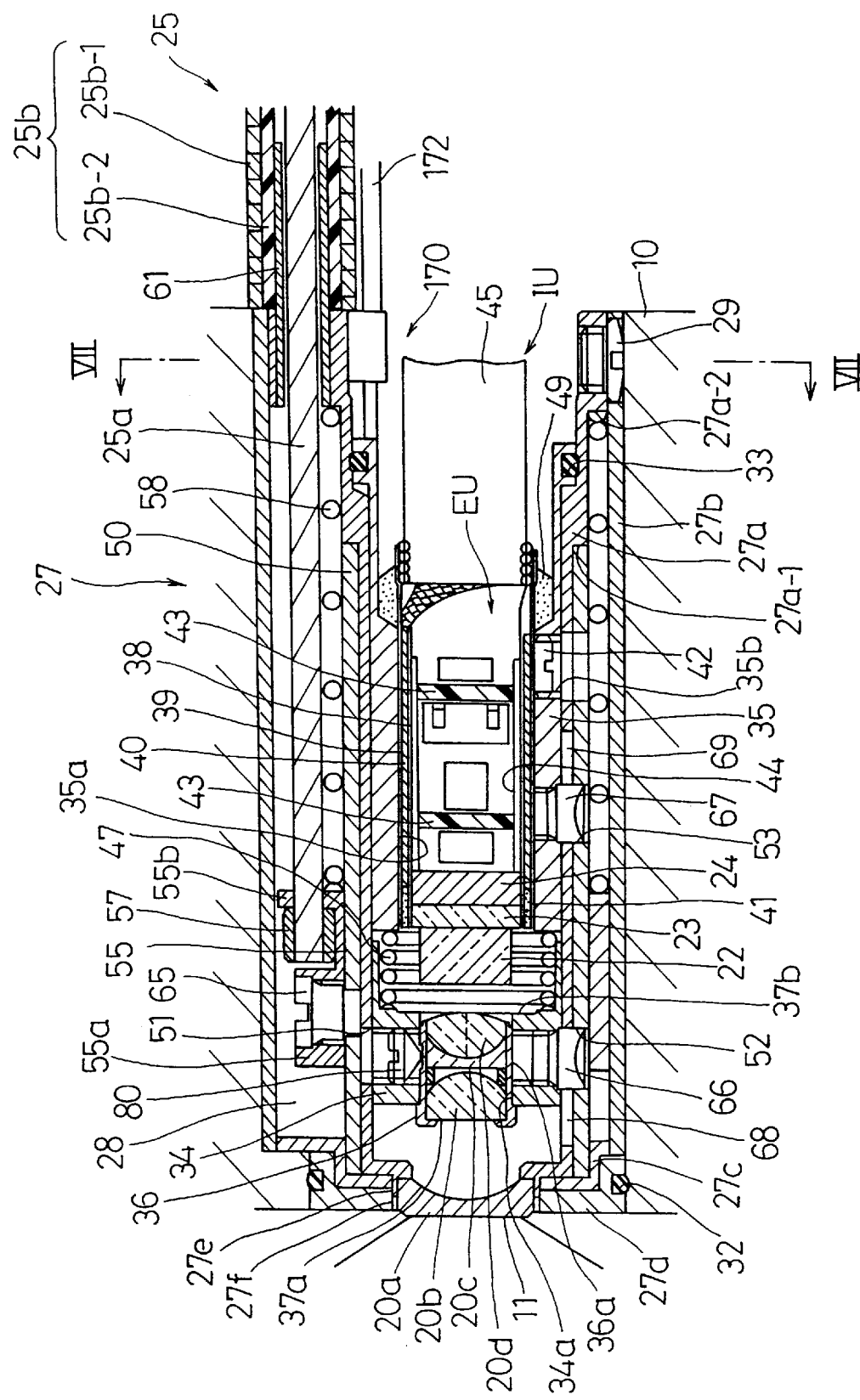
Figure 6:
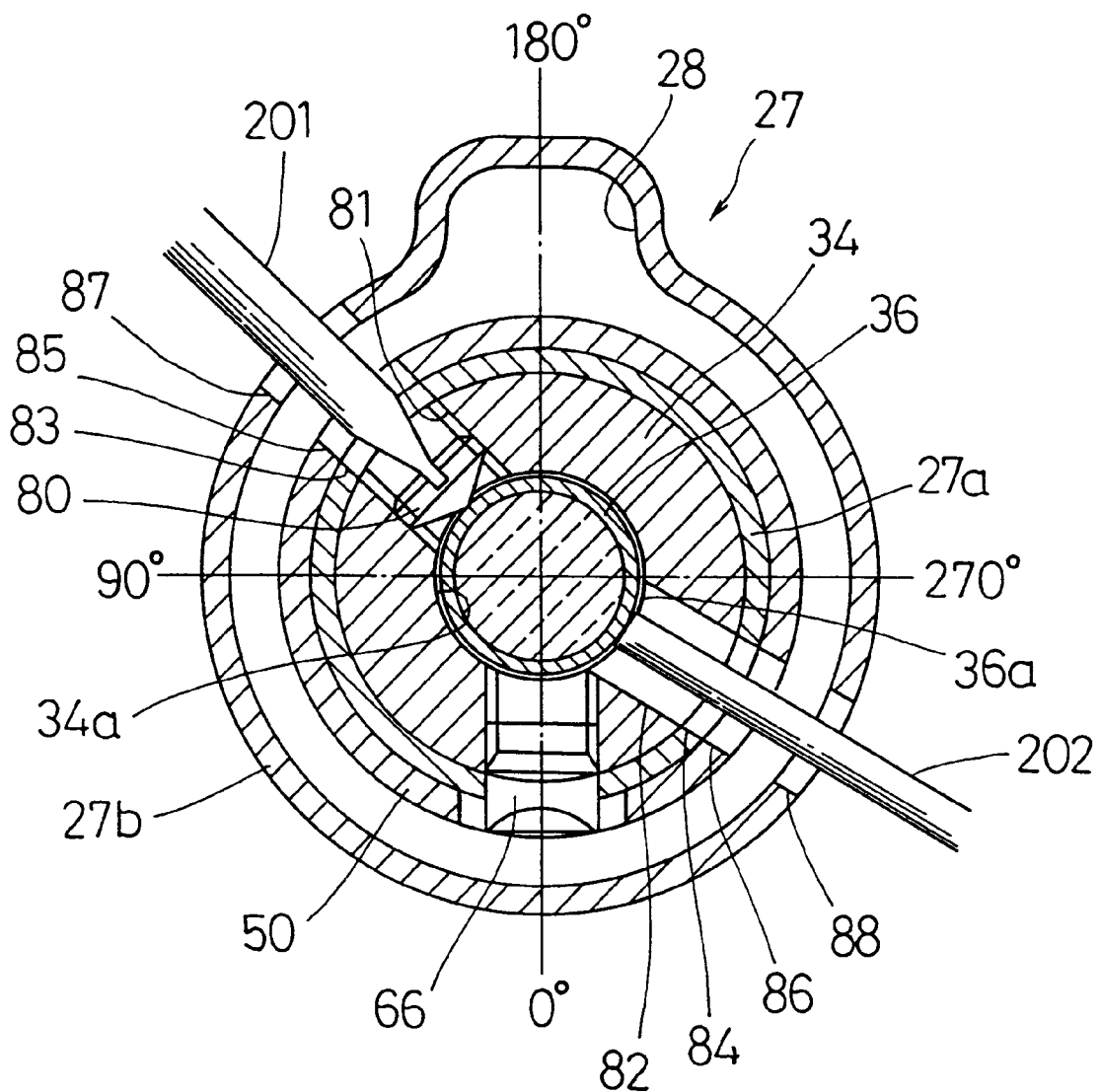
FIG. 6 is a cross-sectional view of the imaging unit IU taken along line VI—VI indicated in FIG. 5b.
Figure 7:
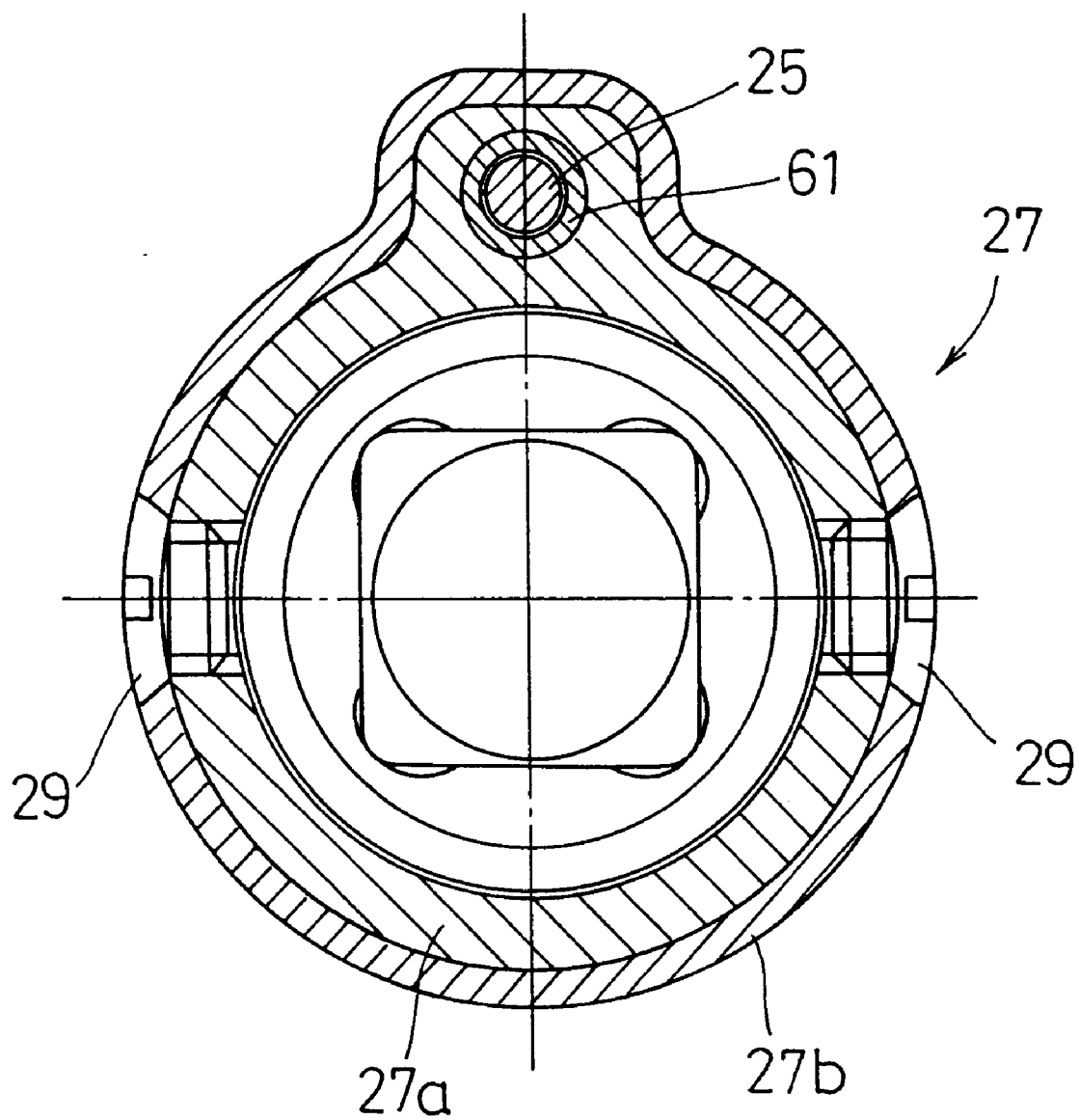
Figure 8B:
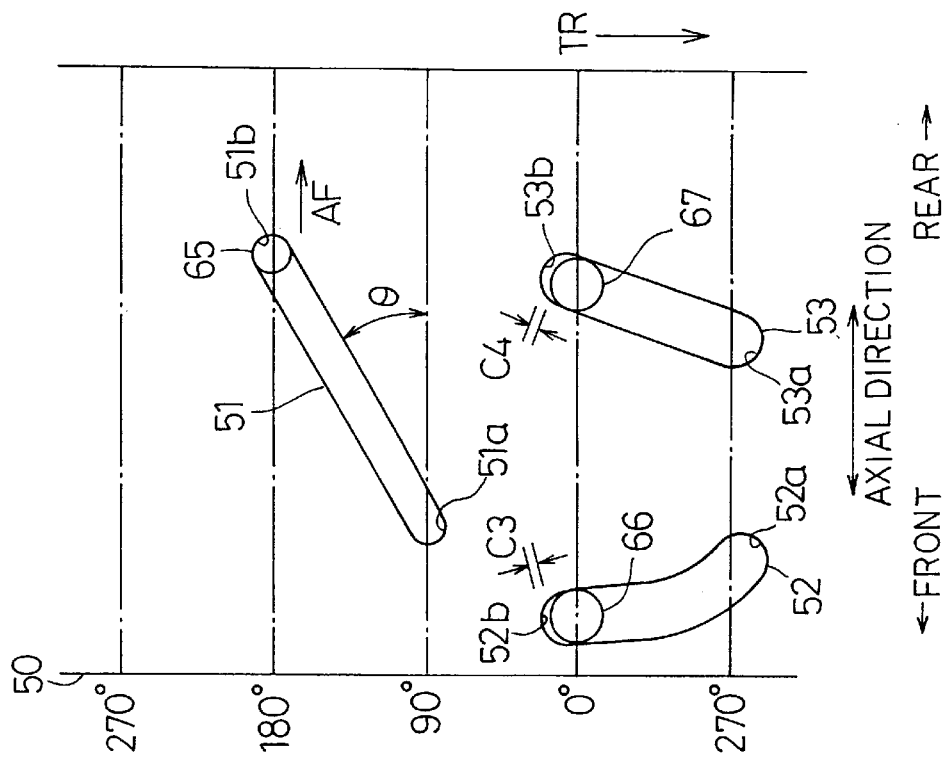
FIGS. 8a and 8b are schematics of the cam cylinder 50 developed into a plane, showing three cam slots formed in the cam cylinder 50 and the associated three pins engaging the cam slots.
Figure 8A:
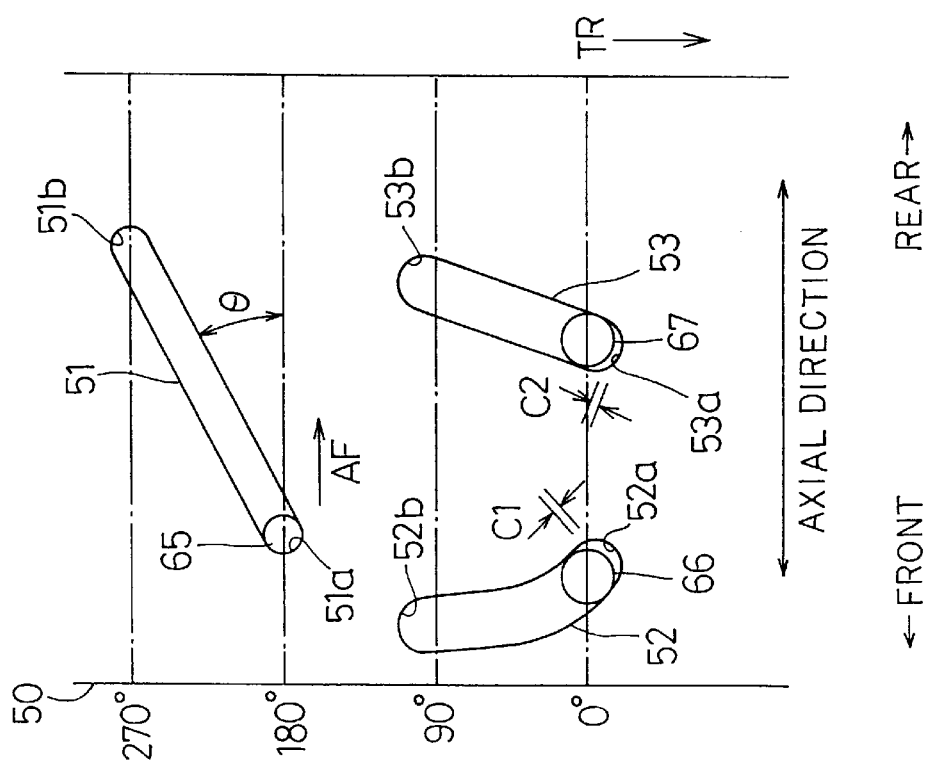

Referring to FIGS. 5a, 5b, 6, 7, 8a and 8b, the imaging unit IU will now be described in more detail. FIGS. 5a and 5b are longitudinal sectional views of the imaging unit IU, showing various components in their positions corresponding to the wide-end and zoom-up-end positions, respectively, of macro-zooming operation. FIG. 6 is a cross-sectional view of the imaging unit IU taken along line VI—VI indicated in FIG. 5b. FIG. 7 is a cross-sectional view of the imaging unit IU taken along line VII—VII indicated in FIG. 5a. FIGS. 8a and 8b are schematics of a cam cylinder developed into a plane, showing three cam slots formed in the cam cylinder and the associated three pins engaging the cam slots.

Generally, the imaging unit IU comprises i) a plurality of optical elements forming an optical system and ii) a support and guide mechanism for supporting and/or guiding the plurality of optical elements. The optical elements includes, among others, i) a certain device having an image-bearing surface on which an image is to be formed and ii) a plurality of lenses arranged along an optical axis for forming an image on the image-bearing surface of the device. In the disclosed embodiment, the device used for this purpose comprises a charge coupled device (CCD) 24. The plurality of lenses comprises a fixed lens 20a and movable lenses 20b, 20c and 20d. Further, the support and guide mechanism is specifically designed to provide macro-zooming function for the imaging unit IU.

In general, the support and guide mechanism of the imaging unit IU used in the disclosed embodiment comprises:

i) a first member 27 fixedly mounted in the housing 10 and including a hollow cylindrical portion 27a having an axis and front and rear ends, the axis of the hollow cylindrical portion being a reference axis and defining an axial direction;

ii) a second member 50 of a hollow cylindrical shape and having a cylindrical surface, the second member 50 being fitted over the hollow cylindrical portion 27a of the first member 27 and being supported and guided for rotational movement about the reference axis with substantially no axial movement relative to the first member 27;

iii) a third member 55 supported and guided for axial movement relative to the first and second members 27 and 50 with substantially no rotational movement about the reference axis, the third member 55 being operatively connected to the distal end of the manipulation cable assembly;

iv) first and second carriages 34 and 35 carrying thereon the movable lenses 20b to 20d and the CCD 24, respectively, the first and second carriages 34 and 35 being supported and guided for axial movement relative to the first and second members 27 and 50 with substantially no rotational movement about the reference axis;

v) a first cam mechanism provided between the second and third members 50 and 55 for producing rotational movement of the second member 50 in response to axial movement of the third member 55; and vi) a second cam mechanism provided between the second member 50 and the first and second carriages 34 and 35 for producing axial movements of the carriages 34 and 35 in response to rotational movement of the second member 50.

More specifically, the imaging unit IU is arranged as follows. The first member 27 is formed as a double-tube member including an inner cylinder 27a and an outer cylinder 27b. The axes of the inner and outer cylinders 27a and 27b extend in parallel to each other. Because the first member 27 is fixedly mounted in the housing 10, either of the cylinders 27a and 27b may be referred to as the "fixed cylinder." However, since the inner cylinder 27a plays greater rolls than the outer cylinder 27b in the support and guide mechanism, the term "fixed cylinder" means the inner cylinder 27a unless explicitly indicated otherwise. Accordingly, the axis of the inner cylinder 27a is a reference axis of the support and guide mechanism and defines an axial direction of the support and guide mechanism. In the following description, the term "axial" refers to the axis of the inner cylinder 27a unless expressly indicated as otherwise.

The inner and outer cylinders 27a and 27b extend in the axial direction and define an annular space between them, in which the second and third members 50 and 55 are received. The inner cylinder 27a has front and rear ends and a thick edge formed at its rear end and projecting radially outwardly to be fitted snug in the outer cylinder 27b. The first member 27 further includes a front end spacer 27c engaging the front ends of the inner and outer cylinders 27a and 27b so as to hold the front ends of the cylinders 27a and 27b in a fixed relationship. The front end spacer 27c and the rear edge of the inner cylinder 27a together serve to define, with precision, an annular space or gap having a constant thickness and extending between the inner and outer cylinders 27a and 27b. The front end spacer 27c is tightly fitted in and over the outer and inner cylinders 27a and 27b, respectively, so as to hermetically seal the front end of the annular space. The inner and outer cylinders 27a and 27b are secured to each other by a pair of set screws 29 (FIG. 7), so that the imaging unit IU may be disassembled by loosening and removing the set screws 29 for repair and/or adjustment if required. The casing 27 further includes a front cap 27d fitted over and covering the front end spacer 27c. The inner cylinder 27b, the front end spacer 27c and the front cap 27d have respective central round openings formed therein, which have nearly the same diameters and are centered to the reference axis, defining together the above mentioned view window 11.

The first member 27 is so designed as to enclose therein all the components of the imaging unit IU in the disclosed embodiment, and thus referred to as the "casing" hereinafter, meaning the casing of the imaging unit IU.

The inner cylinder 27a has first and second shoulders 27a-1 and 27a-2 formed on the outer surface at its rear end. The outer support tube 25b of the manipulation cable assembly 25 has its distal end fixedly secured to the rear end of the casing 27 of the imaging unit IU through a connector pipe 61, which is fixed to the inner cylinder 27a of the casing 27. The inner cable 25a of the manipulation cable assembly 25 enters the casing 27 through the connector pipe 61.

The inner cylinder 27a has first and second axial guide slots 68 and 69 formed therein, which extend in line along a common generator of the cylindrical surface of the inner cylinder 27a. The guide slots 68 and 69 serve to guide the first and second carriages 34 and 35, respectively, for their axial movement as described below in more detail. The outer cylinder 27b has an axial guide groove 28 formed therein, which extends through the entire length of the outer cylinder 27b and opens radially inwardly. The guide groove 28 serves to guide the third member 55 for its axial movement as described below in more detail.

The second member 50 is, as described above, a hollow cylindrical member fitted over the inner cylinder 27a of the casing 27 and supported and guided for rotational movement about the reference axis. In order for smooth and precise operation of the imaging unit IU, the inner surface of the second member 50 and the outer surface of the inner cylinder 27a are finished to be smooth enough to make sliding contact to each other while leaving little allowance between them. Any axial movement of the second member 50 relative to the casing 27 is effectively prevented by the front end spacer 27c and the first shoulder 27a-1 of the inner cylinder 27a, which are in slidable engagement with the front and rear end edges of the second member 50. Thus, the second member 50 is guided to produce substantially no axial movement relative to the casing 27. The second member 50 has three elongated cam slots 51, 52 and 53 formed in its cylindrical wall as illustrated in FIGS. 8a and 8b, and is thus referred to as the "cam cylinder" hereinafter.

In each of FIGS. 8a and 8b, the horizontal and vertical directions correspond to the axial and circumferential directions, respectively, of the cam cylinder 50. Among the three elongated cam slots 51, 52 and 53, the first cam slot 51 is strictly helical in shape and thus extends obliquely with respect to the generators of the cylindrical surface of the cam cylinder 50 in one direction, so as to cut the generators at a constant angle θ. The second and third cam slots 52 and 53 are not strictly but nearly helical in shape and extend obliquely with respect to the generators of the cylindrical surface of the cam cylinder 50 in opposite directions.

The third member 55 is formed as a ring member fitted over and supported by the cam cylinder 50 for sliding movement on the cam cylinder 50. The third member 55 has a first radial projection 55a projecting radially outwardly and received in the axial guide groove 28 of the outer cylinder 27b. The projection 55a and the axial guide groove 28 are in slidable engagement with each other, so that the third member 55 is guided for axial movement on the cam cylinder 50 while prevented from producing rotational movement about the reference axis, or in other words, guided to produce substantially no rotational movement about the reference axis. For achieving macro-zooming operation of the imaging unit IU, the third member 55 is driven by the inner cable 25a of the manipulation cable assembly 25 for sliding movement within the casing 27 in the axial direction, so that the third member 55 is referred to as the "axial slider" hereinafter.

The axial slider 55 has a second radial projection 55b projecting into the axial guide groove 28 of the outer cylinder 27b and having an axial hole formed therein. The distal end of the inner cable 25a of the imaging unit manipulation cable assembly 25 extends axially through the hole and has an anchor collar 57 secured to the tip end thereof. In this manner, the inner cable 25a has its distal end connected to the axial slider 55.

A first compression helical spring 58 is disposed around the cam cylinder 50 between the axial slider 55 and a second shoulder 27a-2 of the inner cylinder 27a for normally urging the axial slider 55 in the axially forward direction. If the proximal end of the inner cable 25a is pulled through the manipulation of the manipulating lever 6 provided on the handpiece HP, the distal end of the inner cable 25a pulls the axial slider 50 in the axially rearward direction against the urging force of the first helical spring 58, so that the axial slider 50 is driven to move in the rearward direction. If the proximal end of the manipulation cable 25 is manipulated to move in the opposite direction, the axial slider 55 is driven by the urging force of the first spring 58 to move in the axially forward direction.

The first cam mechanism provided between the cam cylinder 50 and the axial slider 55 comprises the first cam slot 51 formed in the cam cylinder 50 and a pin 65 provided on and fixedly secured to the axial slider 55. The pin 65 comprises a screw secured to and in threadable engagement with a tapped hole formed in the axial slider 55. The screw or pin 65 has a cylindrical tip end projecting radially inwardly into the first cam slot 51 and in slidable engagement therewith. Since the first cam slot 51 is a strict helical slot, any axial movement of the pin 65 will cause the corresponding rotational movement of the cam cylinder 50, such that the rotational displacement of cam cylinder 50 is in a linear relationship with the axial displacement of the axial slider 55. In this manner, the first cam mechanism produces rotational movement of the cam cylinder 50 in response to axial movement of the axial slider 55. In addition, the first cam mechanism provides another function of determining the end positions of the axial slider 55, which in turn determines the angular stroke of the rotation of the cam cylinder 50. This function is detailed below in conjunction with the second and third cam slots 52 and 53.

The first and second carriages 34 and 35 are formed as generally cylindrical members adapted to be fitted snug in the inner cylinder 27a and supported thereby for axial sliding movement relative to the inner cylinder 27a. The first carriage 34 has a central axial bore 34a for receiving therein a lens holder 36 for holding the movable lenses 20b to 20d. The second carriage 35 has a central axial bore 35a for receiving therein an electronics unit EU including the CCD 24 and the associated circuitries. Accordingly, the first carriage 34 carries thereon the movable lenses 20b to 20d and the second carriage 35 carries thereon the CCD 24. The lens holder 36 and the electronics unit EU are described below in more detail. As shown, the second carriage 35 has an annular groove formed in the outer surface at its rear end, in which an O-ring 33 is received for sealing the gap between the outer surface of the second carriage 35 and the inner surface of the inner cylinder 27a.

The first and second carriages 34 and 35 are provided with pins 66 and 67, respectively, fixedly secured thereto. Each of the pins 66 and 67 has a cylindrical head and a threaded shank. The threaded shank is in threadable engagement with a tapped hole formed in the corresponding carriage and the cylindrical head projects radially outwardly from the corresponding carriage.

The pins 66 and 67 (more strictly, the cylindrical heads of the pins 66 and 67) extend through the first and second axial guide slots 68 and 69, respectively, formed in the inner cylinder 27a, and are in slidable engagement with these axial guide slots 68 and 69. The pins 66 and 67 further extend into the second and third cam slots 52 and 53, respectively, formed in the cam cylinder 50, and are in slidable engagement with these cam slots 52 and 53.

By virtue of the slidable engagement of the pin 66 provided on the first carriage 34 with the corresponding axial guide slot 68 formed in the inner cylinder 27a, the first carriage 34 is guided for axial movement in the inner cylinder 25a with substantially no rotational movement about the reference axis. Similarly, by virtue of the slidable engagement of the pin 67 provided on the second carriage 35 with the corresponding axial guide slot 69 formed in the inner cylinder 27a, the second carriage 35 is guided for axial movement in the inner cylinder 25a with substantially no rotational movement about the reference axis.

On the same time, the pins 66 and 67 and the cam slots 52 and 53 together form the second cam mechanism provided between the cam cylinder 50 and the first and second carriages 34 and 35. Since the cam slots 51 and 52 are nearly helical, rotational movement of the cam cylinder 50 will produce the corresponding axial movements of the carriages 34 and 35 on which the pins 66 and 67 are provided, and each of the axial displacements of the carriages 34 and 35 is in a predetermined relationship with the axial displacement of the cam cylinder 50. In this manner, the second cam mechanism will produce axial movements of the carriages 34 and 35 in response to rotational movement of the cam cylinder 50.

In order to achieve precise positioning of the first and second carriages 34 and 35, a second compression helical spring 47 is provided between the first and second carriages 34 and 35 for normally urging them in axially opposite directions apart from each other. By virtue of the provision of the second helical spring 47, each of the pins 66 and 67 is urged against and kept in contact with one side edge ("external side edge" with reference to the center of the second helical spring 47) of the corresponding cam slot (52 or 53), so that any undesirable effects of the inevitable allowance between each of the pins 66 and 67 and the side edges of the corresponding cam slot (52 or 53) may be effectively eliminated, resulting in precise positioning of the first and second carriages 34 and 35.

Because the pins 66 and 67 are normally urged by the second helical spring 47 against the external side edges of the cam slots 52 and 53, respectively, the pins 66 and 67 are normally pushing the external side edges of the corresponding cam slots 52 and 53. On the other hand, the cam slots 52 and 53 extend, as described above, obliquely with respect to the generators of the cylindrical surface of the cam cylinder 50. Therefore, each of the push forces acting from the pins 66 and 67 onto the corresponding external side edges of the cam slots 52 and 53, respectively, may be broken into axial and circumferential components, in which each of the circumferential components of the push forces will serve as a torque tending to rotate the cam cylinder 50 about its axis. Further, because the cam slots 52 and 53 are urged in opposite directions to each other through the second helical spring 47 while they are inclined in opposite directions, so that the circumferential components of the push forces have the same direction. Thus, the resultant torque of these torques (or the circumferential components of the push forces) equals the sum of these torques. The resultant torque is designated by TR and shown in FIGS. 8a and 8b. As clearly understood from the above, the torque TR i) is produced from the urging force of the second compression helical spring 47 through the second cam mechanism, ii) normally acts on and tends to rotate the cam cylinder 50 in one direction (counter-clockwise direction as viewed from the rear end of the cam cylinder 50) and iii) varies depending on the angular displacement of the cam cylinder 50.

Moreover, because the torque TR tends to rotate the cam cylinder 50, one side edge ("external side edge" with reference to the center of the first helical spring 58) of the first cam slot 51 is urged against and kept in contact with the corresponding pin 65 provided on the axial slider 55, so that any undesirable effects of the inevitable allowance between the pin 65 and the side edge of the first cam slot 51 may be effectively eliminated, which also contributes to precise positioning of the first and second carriages 34 and 35.

Again, the pin 65 and the external side edge of the first cam slot 51 are normally pushing each other by means of the torque TR, while the cam slot 51 extends obliquely with respect to the generators of the cylindrical surface of the cam cylinder 50, so that the push force acting from the external edge of the first cam slot 51 onto the pin 65 may be broken into axial and circumferential components, in which the axial component of the push force will serve as an axial force tending to move the axial slider 55 in the rearward direction. This axial force is designated by AF and shown in FIGS. 8a and 8b. As clearly understood from the above, the axial force AF i) is produced from the torque TR through the first cam mechanism, ii) normally acts on and tends to move the axial slider 55 in the axially rearward direction and iii) varies depending on the torque TR.

As described above, the axial slider 55 is normally urged in the axially forward direction by the first compression helical spring 58. As one aspect of the present invention, the urging force acting from the first spring 58 onto the axial slider 55 in the axially forward direction is chosen to be greater than the axial force AF acting from the cam cylinder 50 onto the axial slider 55 in the axially rearward direction at any time. (The term "at any time" is used in order to take account of the fact that the urging force of the first spring 58 varies depending on the axial displacement of the axial slider 55 as well as the axial force AF varies depending on the torque TR.) Accordingly, the minimum value of the axial force acting on the axial slider 55 from the first spring 58 is chosen to be greater than the maximum value of the axial force AF acting on the axial slider 55 from the cam cylinder 50. By virtue of this, the resultant axial force of these two axial forces acting in opposite directions will act on the axial slider 55 so as to tend to move it in the axially forward direction. As apparently understood, when the axial slider 55 is in any of its possible axial positions except the foremost and rearmost positions, the resultant axial force acting on the axial slider 55 substantially equals the pull force acting from the axial slider 55 onto the distal end of the inner cable 25a.

Referring in particular to FIGS. 8a and 8b, the shapes of the cam slots 51, 52 and 53 are described in more detail. As described, the optical elements of the imaging unit IU include, among others, the fixed lens 20a, the movable lenses 20b to 20d and the CCD 24. The fixed lens 20a is fixed to the casing 27, while the movable lenses 20b to 20d and the CCD 24, being carried on the first and second carriages 34 and 35, are movable relative to the casing 27 in the axial direction (i.e., along the optical axis). The support and guide mechanism provides axial movements of the first and second carriages 34 and 35 with a predetermined relationship established between them, so as to provide macro-zooming function, for which each of the first and second carriages 34 and 35 are moved between wide-end and zoom-up-end positions. The shapes of the second and third cam slots 52 and 53 are designed to achieve such axial displacements of the first and second carriages 34 and 35.

More specifically, the shape of the first cam slot 51 shows two features of the present invention.

First, in order to achieve smooth rotation of the cam cylinder 50 with a relatively small force acting from the axial slider 55 (more strictly, from the pin 65 provided on the axial slider 55) onto the cam cylinder 50, the angle θ formed between a generator of the cylindrical surface of the cam cylinder 50 and the first cam slot 51 is preferably equal to or less than 45 degrees. On the other hand, the smaller the angle θ is, the longer the first cam slot 51 has to be for the same angular stroke of the cam cylinder 50. Accordingly, it is preferable that the angle θ is chosen to fall in a range from 10 to 45 degrees. It is noted that the angle θ in this range will permit not only smooth operation of the imaging unit IU but also the use of a helical spring made of a steel wire of relatively small diameter for the first compression helical spring 58, which contributes to downsizing of the imaging unit IU. In the disclosed embodiment, the angle θ is chosen to be about 30 degrees, while providing the angular stroke of the cam cylinder 50 of 90 degrees.

Second, the first cam slot 51 is designed such that the foremost and rearmost positions of the axial slider 55 are defined by the shape or geometry of the first cam slot 51. More specifically, the axially forward displacement of the axial slider 55 is limited by the abutment of the pin 65 provided on the axial slider 55 against the front end edge 51a of the first cam slot 51, with a clearance C1 remaining between the pin 66 provided on the first carriage 34 and one end edge 52a of the corresponding (or second) cam slot 52, as well as a clearance C2 remaining between the pin 67 provided on the second carriage 35 and one end edge 53a of the corresponding (or third) cam slot 53, as shown in FIG. 8a. Similarly, the axially rearward displacement of the axial slider 55 is limited by the abutment of the pin 65 against the rear end edge 51b of the first cam slot 51, with a clearance C3 remaining between the pin 66 and the other end edge 52b of the corresponding cam slot 52, as well as a clearance C4 between the pin 67 and the other end edge 53b of the cam slot 53, as shown in FIG. 8b. Thus, the first cam slot 51 serves as a stop mechanism for limiting the axial displacement of the axial slider 55. This directly leads to the fact that the first cam slot 51 also serves as a stop mechanism for limiting the rotational displacement of the cam cylinder 50 so as to determine the angular stroke of the cam cylinder 50, which is 90 degrees as described above. Thus, by virtue of the above arrangement, neither an additional stop mechanism for limiting the axial displacement of the axial slider 55 nor an additional stop mechanism for limiting the rotational displacement of the cam cylinder 50 is needed, resulting in a simple construction of the imaging unit IT.

In operation, when the cam cylinder 50 has been rotated to reach the angular position indicated in FIG. 8a, the first carriage 34 provided with the pin 66 is located in its rearmost position and the second carriage 35 provided with the pin 67 in its foremost position, as shown in FIG. 5a, and thus the group of the movable lenses 20b to 20d in its rearmost position and the CCD 24 in its foremost position. This geometry of the optical system provides an angle of view of 120 degrees with a depth of field from 5 to 100 mm, which corresponds to the wide-end position of the imaging unit IU.

On the other hand, when the cam cylinder 50 has been rotated to reach the angular position indicated in FIG. 8b, the group of the movable lenses 20b to 20d carried on the first carriage 34 is in its foremost position and the CCD 24 carried on the second carriage 35 is in its rearmost position, as shown in FIG. 5b. This geometry of the optical system provides an angle of view of 40 degrees with a depth of field from 2 to 4 mm, which corresponds to the zoom-up-end position of the imaging unit IU.

Depending on the position of the manipulation lever 6 selected by the user, the first and second carriages 34 and 35 may be located at any position between their foremost and rearmost positions with a predetermined relationship established between them by means of the shapes or geometries of the second and third cam slots 52 and 53, so that the angle of view and the depth of field may be continuously varied as desired by the user. In this manner, macro-zooming operation is provided for the imaging unit IU.

In view of the fact that axial movement of the axial slider 55 causes rotational movement of the cam cylinder 50, which in turn causes axial movement of the carriages 34 and 35, the first cam slot 51 may be referred to as the "input cam slot" and the second and third cam slots 52 and 53 as the "output cam slots".

Figure 9:
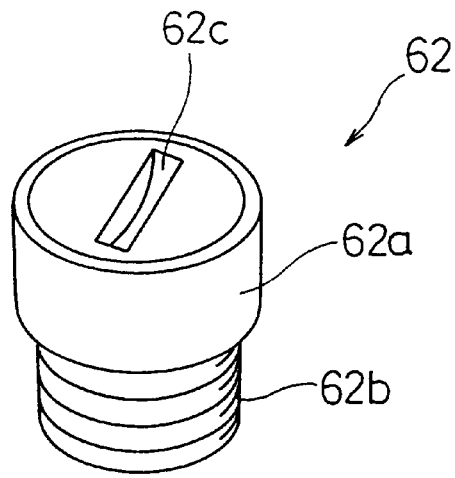
FIG. 9 shows a pin 62 which is used in the disclosed embodiment as each of the pins 66 and 67 shown in FIGS. 8a and 8b among others.
Figure 10:
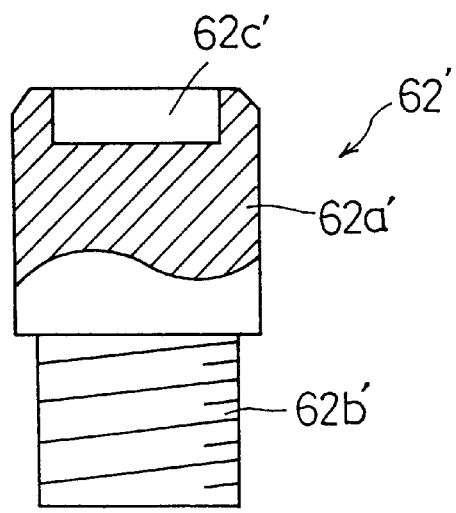
FIG. 10 shows a pin 62' as an alternative example which may be used in place of the pin 62 of FIG. 9; and 67 shown in FIG. 8a and 8b.

Referring next to FIGS. 9 and 10, preferred examples for the pins 66 and 67 will be described. FIG. 9 shows a pin 62 which is used in the disclosed embodiment as each of the pins 66 and 67. FIG. 10 shows a pin 62' as an alternative example which may be used in place of the pin 62 of FIG. 9. The pin 62 comprises a cylindrical head 62a having an axis and a circumferential surface adapted for engagement with the associated elongated cam slot, and a threaded shank 62b coaxial with the cylindrical head 62a. The head 62a further has an elongated recess 62c formed therein at the top surface thereof and extending diametrically. The elongated recess 62c is adapted to receive therein the tip end of a minus-type screwdriver. The elongated recess 62c has a semicircular cross-section as taken along a plane which contains the axis of the cylindrical head 62a and extends in the longitudinal direction of the elongated, diametrical recess 62c. It is important that the elongated recess 62c has both ends not reaching the circumferential surface of the cylindrical head 62a. Accordingly, the cylindrical head 62a has a complete circumferential surface with no cutout formed in that surface. Conventional pins with a cylindrical head used for this purpose usually have an elongated slot extending diametrically and entirely across the top surface of the cylindrical head, so that the cylindrical head has an incomplete circumferential surface with two cutouts formed therein at the ends of the slot. The edges of the cutouts, however, affects the smooth slidable engagement of the head with the corresponding cam slot. The pin 62 is free from such drawback, by virtue of the elongated recess not reaching the circumferential surface of the cylindrical head 62a. The pin 62' in FIG. 10 comprises a cylindrical head 62a' having an axis and a circumferential surface adapted for engagement with the associated elongated cam slot, and a threaded shank 62b' coaxial with the cylindrical head 62a'. The head 62a' further has an elongated recess 62c' formed therein at the top surface thereof and extending diametrically. The pin 62' differs from the pin 62 in that the elongated recess 62c' has a rectangular cross-section as taken along a plane which contains the axis of the cylindrical head 62a' and extends in the longitudinally direction of the elongated, diametrical recess 62c'. Again, the recess 62c' has both ends not reaching the circumferential surface of the cylindrical head 62a'. Except the cross-section of the recess 62c', the pin 62' of FIG. 10 has the same geometrical features as the pin 62 of FIG. 9. Thus, either pin can contribute to smooth operation of the first and second carriages 34 and 35.

Referring again to FIGS. 5a, 5b, 6 and 7, it will be described in detail how the support and guide mechanism shown above supports and/or guides the optical elements used in the imaging unit IU. As mentioned above, the optical elements include the fixed lens 20a, the movable lenses 20b to 20d and the CCD 24, all of which are disposed along a straight line defining the optical axis of the optical system of the imaging unit IU, which is capable of providing macro-zooming function. In the disclosed embodiment, the optical axis is coincident with the reference axis mentioned above.

For receiving the fixed lens 20a, the casing 27 has a front circular opening 27e which is coaxial with the optical axis.

Further, the front cap 27d, which is tightly fitted over the front end member 27c of the casing 27 as describe above, has a circular opening 27f which is also coaxial with the optical axis. The fixed lens 20a is tightly fitted in the front opening 27e of the casing 27 with a small clearance or gap left between the outer peripheral edge of the fixed lens 20a and the edge of the front cap opening 27f. This gap is filled with hard and adhesive curable-sealant having a composition similar to that of a certain epoxy resin adhesive. By virtue of this arrangement, any leakage of fluid or gas into or out of the casing 27 through the region around the fixed lens 20a is effectively prevented. Further, the front cap 31 has an annular groove formed in the outer circumferential surface thereof, in which an O-ring 32 is received for sealing the gap between the front cap 31 and the housing 10.

The movable lenses 20b to 20d form a single lens group and are received in and fixedly held by the lens holder 36. In addition, a fixed aperture stop 37a and a field stop 37b are held by the lens holder 36 and disposed in front of and at the back of the group of lenses 20b to 20d, respectively. The lens holder 36 is of a hollow cylindrical shape and has an outer circumferential surface. The lens holder 36 is formed to be fitted snug in the central axial bore 34a of the first carriage 34 for axial displacement relative to the carriage 34. Further, the lens holder 36 has an annular groove 36a formed in its outer circumferential surface. As clearly shown in FIG. 6, the first carriage 34 has a set-screw-receiving hole 81 and an adjustment-tool-access hole 82, both extending radially through the wall of the first carriage 34 and in communication with the central axial bore 34a. A set screw 80, received in and in threadable engagement with the set-screw receiving hole 81, is used to fixedly secure the lens holder 36 to the first carriage 34. A screwdriver 201 is shown rotating the set screw 80. The adjustment-tool-access hole 82 allows the access to the annular groove 36a of the lens holder 36 by the tip end of a bar-like adjustment tool 202. Also, the inner cylinder 27a has a screwdriver-access hole 83 and an adjustment-tool-access hole 84. The cam cylinder 50 has a screwdriver-access hole 85 and an adjustment-tool-access hole 86. The outer cylinder 27b has a screwdriver-access hole 87 and an adjustment-tool-access hole 88. The three screwdriver-access holes 83, 85 and 87 are formed at such positions that they will be in alignment with the set-screw-receiving hole 81 when the first carriage 34 is in its foremost position and the cam cylinder 50 is in the corresponding angular end position, while at the same time the four adjustment-tool-access holes 82, 84, 86 and 88 will be in alignment with each other. Thus, with the first carriage 34 in its foremost position (or zoom-up-end position), adjustment for acceptable focusing state may be performed when required, by loosening the set screw 80 by a screwdriver 201, displacing the lens holder 36 in an appropriate axial direction relative to the first carriage 34 by manipulating the annular groove 36a of the lens holder 36 by the tip end of an adjustment tool 202 engaging said annular groove 36a, and then tightening again the set screw 80 to fixedly secure the lens holder 36 to the first carriage 34.

The electronics unit EU including the CCD 24 and the associated circuitries has a generally cylindrical shape adapted to be fitted snug in the central axial bore 35a of the second carriage 35. The circuitries associated with the CCD 24 include a driver circuitry, a signal processing circuitry and others. The electronics unit EU is provided with a electromagnetic shield in order to improve the quality of the video signals transmitted.

More specifically, the electronics unit EU comprises a flexible printed circuit board 44 on which the CCD 24 is mounted. The flexible printed circuit board 44 comprises a flexible substrate such as one used for the tape automated boning technology. The CCD 24 is disposed at the front end of the circuit board 44, with its image-sensing surface facing forward. The image-sensing surface is an image-bering surface on which an image is to be formed. The CCD 24 has a cover plate of glass 23 attached on and covering the image-sensing surface of the CCD 24. A YAG-laser-radiation cut filter 22 is attached in front of the cover plate 23 to protect the CCD 24 from the damage which could be otherwise caused by the radiation from a YAG-laser knife when it is used. The flexible circuit board 44 also has two sub-boards 43 mounted thereon, on which the circuitries associated with the CCD 24 are mounted. A video signal transmitting cable 45 is connected to the electronics unit EU. The cable 45 comprises a length of shielded cable including a plurality of inner conductors and a shielding conductor surrounding the inner conductors. The inner conductors are electrically connected to the conductors provided on the flexible circuit board 44.

The flexible circuit board 44 is rolled into a generally cylindrical form with a diameter substantially the same as the diameter of the CCD 24. A length of thin, elongated electrically-insulative tape is wrapped around the roll of the circuit board 44 in a lot of turns to form a first insulative layer 38 extending over the entire length of the roll. Over the roll thus insulated with the first insulative layer 38, a shield pipe 40 is fitted, which is of a hollow cylindrical shape and made of a suitable electrically-conductive material such as a metal. The front edge of the shield pipe 40 reaches a position a little behind the front surface of the cover plate 23 of the CCD 24 and is covered by electrically-insulative layer 41 of epoxy resin material having a composition similar to that of a certain epoxy resin adhesive. Again, a length of thin, elongated electrically-insulative tape is wrapped around the outer surface of the shield pipe 40 to form a second insulative layer 39 extending over the entire length of the shield pipe 40.

The shield pipe 40 is electrically connected to the shielding conductor of the shielded cable 45. As clearly understood from the above, the first insulative layer 38 provides insulation between the circuit board 44 and the shield pipe 40 while the second insulative layer 39 provides insulation between the shield pipe 40 and the second carriage 35. By virtue of these insulation, no current of the video signal flowing in the electronics unit EU may leak into any components of the support and guide mechanism of the imaging unit IU nor into the inner cable 25a connected to the support and guide mechanism. If such current leak would occur, the inner cable 25a could radiate electromagnetic waves, which in turn could produce severe interferences or to any sensitive electronic equipment simultaneously used in the environment of the endoscope ES.

Figure 11:
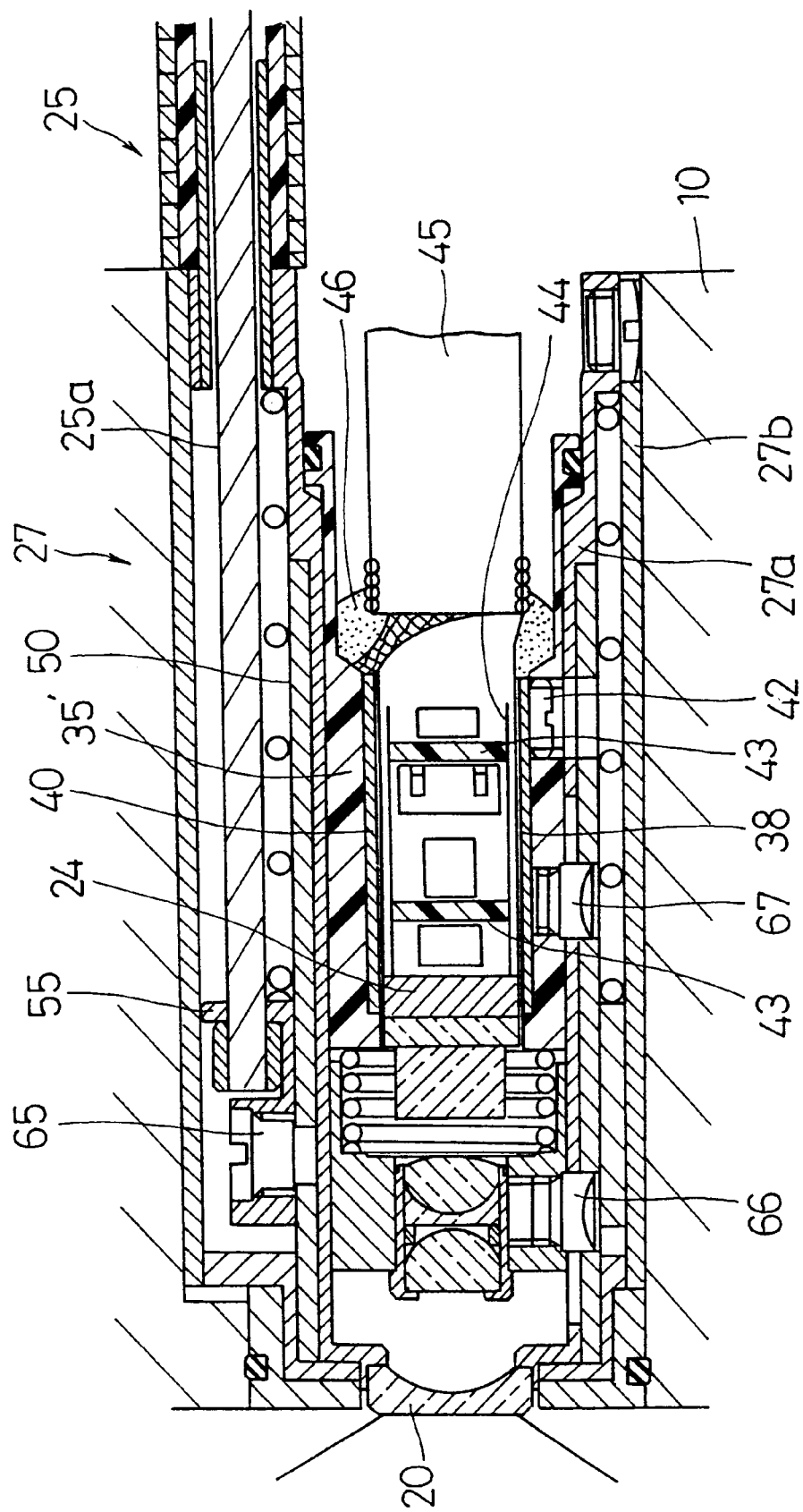
FIG. 11 shows an alternative arrangement for the second carriage 35 and the electronics unit EU shown in FIGS. 5a and 5b.

FIG. 11 shows an alternative arrangement for the second carriage 35 and the electronics unit EU shown and described above. In FIG. 11, the same components as shown in FIGS. 5a and 5b are designated by the same reference numerals and not described for simplicity. In FIG. 11, a second carriage 35' differs from the second carriage 35 of FIGS. 5a and 5b in that the carriage 35' is made of electrically-insulative material such as a plastic. Since the insulative carriage 35' provides insulation of the shield pipe 40 from the components of the support and guide mechanism of the imaging unit IU, the second insulation layer 39 and the front end insulation layer 41 are eliminated. This arrangement enjoys the same advantages as the arrangement of FIGS. 5a and 5b.

In either case, the electronics unit EU, having a generally cylindrical shape, is fitted snug in the central axial bore 35a of the second carriage 35 or 35' for axial displacement relative to the carriage 35 or 35'. Since both types of the second carriages 35 and 35' support the electronics unit EU in the same manner, the following description refers only to the carriage 35 of FIGS. 5a and 5b.

The second carriage 35 has a set-screw-receiving hole 35b extending radially through the wall of the carriage 35 and in communication with the central axial bore 35a of the carriage 35. A set screw 42, received in and in threadable engagement with the set-screw-receiving hole 35b, is used to secure the electronics unit EU to the second carriage 35. Because the set screw 42 is used for securing the electronics unit EU, fine adjustment for the axial position of the electronics unit EU relative to the second carriage 35 may be performed by i) loosening the set screw 42, displacing the electronics unit EU in an appropriate axial direction relative to the second carriage 35, checking the image quality for acceptable focusing states at both the wide-end and zoom-up-end positions, and then tightening again the set screw 42 to fixedly secure the electronics unit EU to the second carriage 35.

After the completion of such adjustment, suitable curable-sealant of a silicone-rubber 49 may be applied to the gap between the outer surface of the rear end of electronics unit EU and the inner surface of the second carriage 35 to form an elastic layer in order to prevent any debris from entering the gap.

Figure 12:
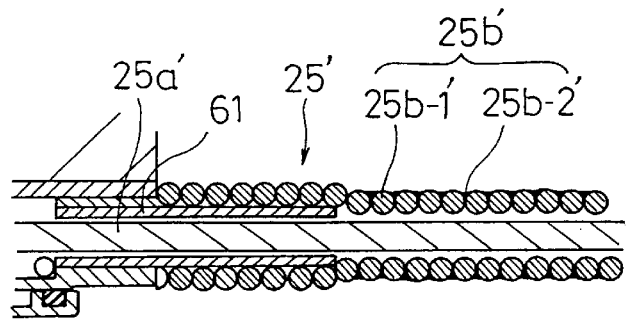
FIG. 12 shows an imaging unit manipulation cable assembly 25' according to a first alternative example.
Figure 13A:
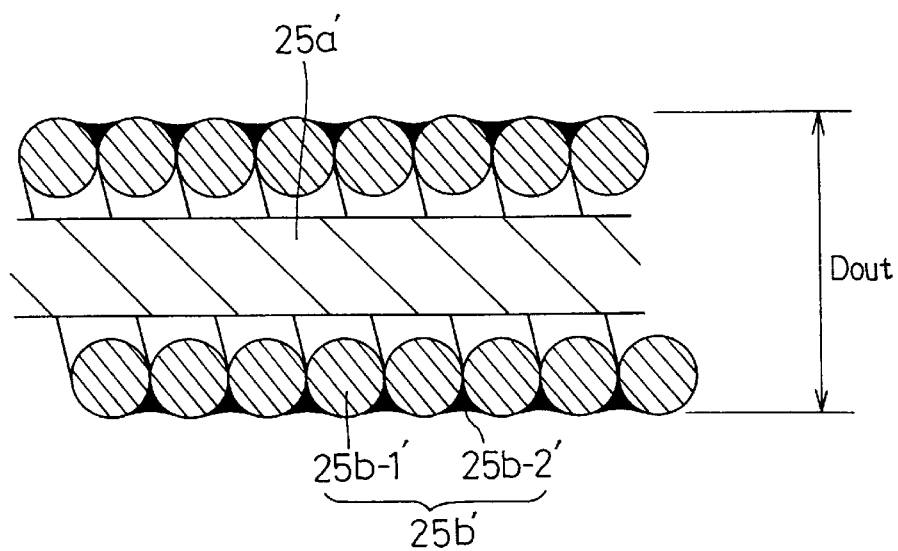
FIGS. 13a and 13b are enlarged longitudinal sectional views of a part of the cable assembly 25' of FIG. 12, showing that part in straight and curved states, respectively.
Figure 13B:
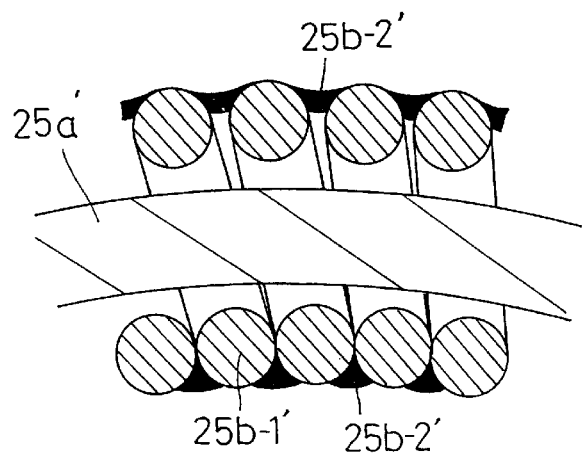
Figure 14:
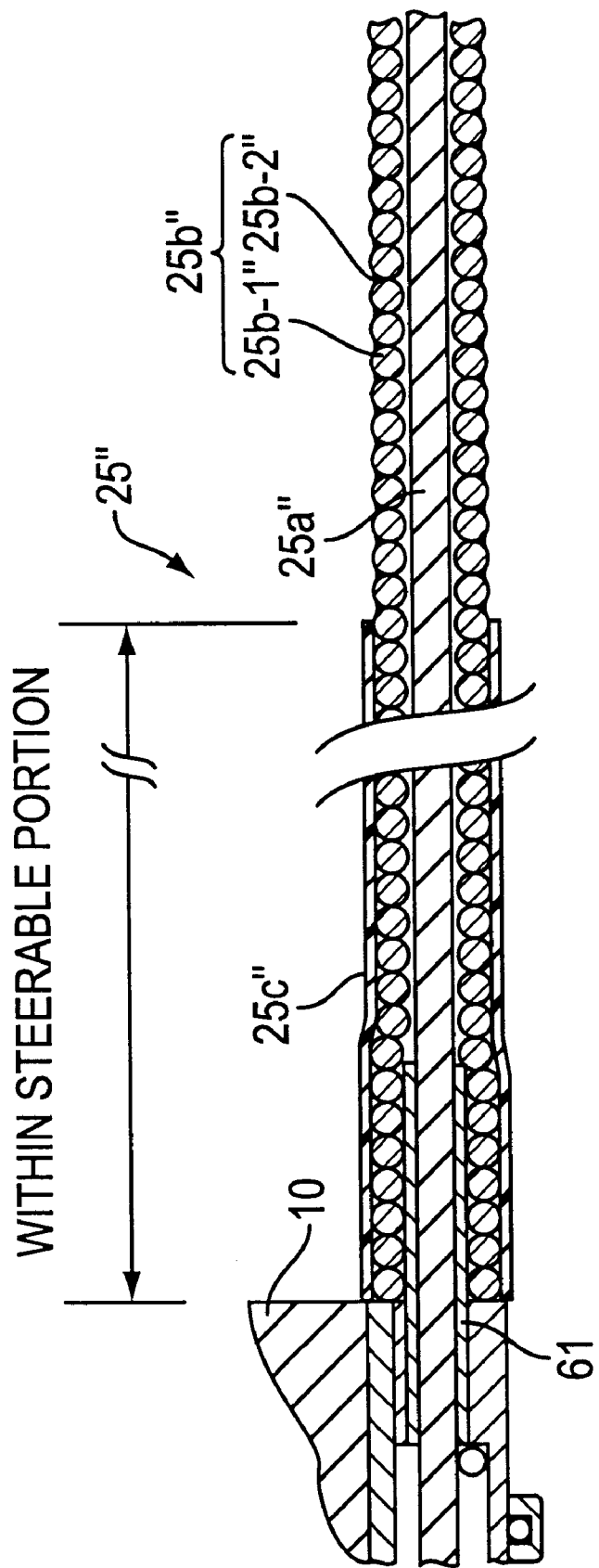
FIG. 14 shows an imaging unit manipulation cable assembly 25" according to a second alternative example.

Referring next to FIGS. 12, 13a, 13b and 14 together with FIGS. 5a and 5b, the imaging unit manipulation cable assembly 25 and two alternative examples thereof will be described in detail. FIG. 12 shows an imaging unit manipulation cable assembly 25' according to a first alternative example. FIGS. 13a and 13b are enlarged longitudinal sectional views of a part of the cable assembly 25' of FIG. 12, showing that part in straight and curved states, respectively. FIG. 14 shows an imaging unit manipulation cable assembly 25" according to a second alternative example.

The imaging unit manipulation cable assembly 25 of FIGS. 5a and 5b comprises, as described above, the outer support tube 25b and the inner cable 25a received therein. The outer support tube 25b comprises a coiled steel wire tube 25b-1 and a resin tube 25b-2 received in and attached to the inner surface of the coiled steel wire tube 25b-1. The coiled steel wire tube 25b-1 comprises a length of square stainless-steel wire coiled closely (meaning that any two adjacent coils are in contact to each other when no external force is applied to the outer support tube 25b) like a closely coiled extension helical spring. Thus, the outer support tube 25b is bendable but stiff against the longitudinal compression force. The resin tube 25b-2 is made of a suitable, elastic or stretchable, resin material and serves to separate the inside of the outer support tube 25b from the outside in order to prevent any debris such as lubricant particles from being introduced into the casing 27 by the inner cable 25a being moved into and out of the casing 27.

The imaging unit manipulation cable assembly 25' of FIG. 12 is usable in place of the cable assembly 25 of FIGS. 5a and 5b. The cable assembly 25' of FIG. 12 includes an inner cable 25a' and an outer support tube 25b'. The inner cable 25a' is the same as the inner cable 25a of FIGS. 5a and 5b described above. The outer support tube 25' comprises a coiled steel wire tube 25b-1' formed by closely coiling a length of round stainless-steel wire (i.e., a stainless-steel wire having a circular cross-section) like a closely coiled extension helical spring, so that it is bendable but stiff against the longitudinal compression force. Highly elastic and strongly adhesive curable-sealant 25b-2' of a silicone-rubber, having a composition similar to that of a certain silicone-rubber adhesive, is applied to the outside of the coiled steel wire tube 25b-1' between adjacent coils thereof. The sealant is highly elastic and strongly adhered to the coils after curing, so that it effectively separate the inside of the coiled steel wire tube 25b-1' from the outside while maintaining the bendability of the coiled steel wire tube 25b-1'.

The amount of the sealant 25b-2' applied is selected such that when the coiled steel wire tube 25b-1' is not curved, the surface of the sealant 25b-2' is recessed from the imaginary cylindrical surface defined by the outer diameter of the coiled steel wire tube 25b-1' as indicated by $D_{out}$ in FIG. 13a. This is important because when the coiled steel wire tube 25b-1' is curved as shown in FIG. 13b, the sealant 25b-2' in the areas inner side of the curving will rise or expand radially outwardly of the coiled steel wire tube 25b-1. If the surface of the sealant 25b-2' were not recessed but filled up the space within the outer diameter $D_{out}$ when the coiled steel wire tube 25b-1' is in straight (not curved) state, the rise or expansion would lead to undesirable increase in the outer diameter of the manipulation cable assembly.

The outer support tube 25b' may be connected to the casing 27 in the same manner as the outer support tube 25b of FIGS. 5a and 5b, i.e., by using a connector pipe 61 as shown in FIG. 12. It may be preferable that the portion of the outer support tube 25b' that is fitted over the connector pipe 61 has no sealant applied thereto for easier fitting of the outer support tube 25b' over the connector pipe 61.

The cable assembly 25" of FIG. 14 is a modification of the cable assembly 25' of FIG. 12 and includes an outer support tube 25b" which is the same as the outer support tube 25b' of FIG. 12 except for the portion thereof that is housed within the steerable portion 4 of the insertion tube IT. This portion of the outer support tube 25b" has no sealant applied to the coiled steel wire tube 25b-1" but instead a flexible cover tube 25c" fitted over the coiled steel wire tube 25b-1", although the transitional region, small in length, has the sealant applied to it as well as the cover tube 25c" fitted over it. The flexible cover tube 25c" has a thin and elastic wall made of a suitable resin material such as polytetrafluoroethylene, so that the portion of the outer support tube 25b" within the steerable portion 4 of the insertion tube IT is more flexible or bendable than the remaining portion, while the inside of the outer support tube 25b" is safely separated from the outside thereby.

Figure 15:
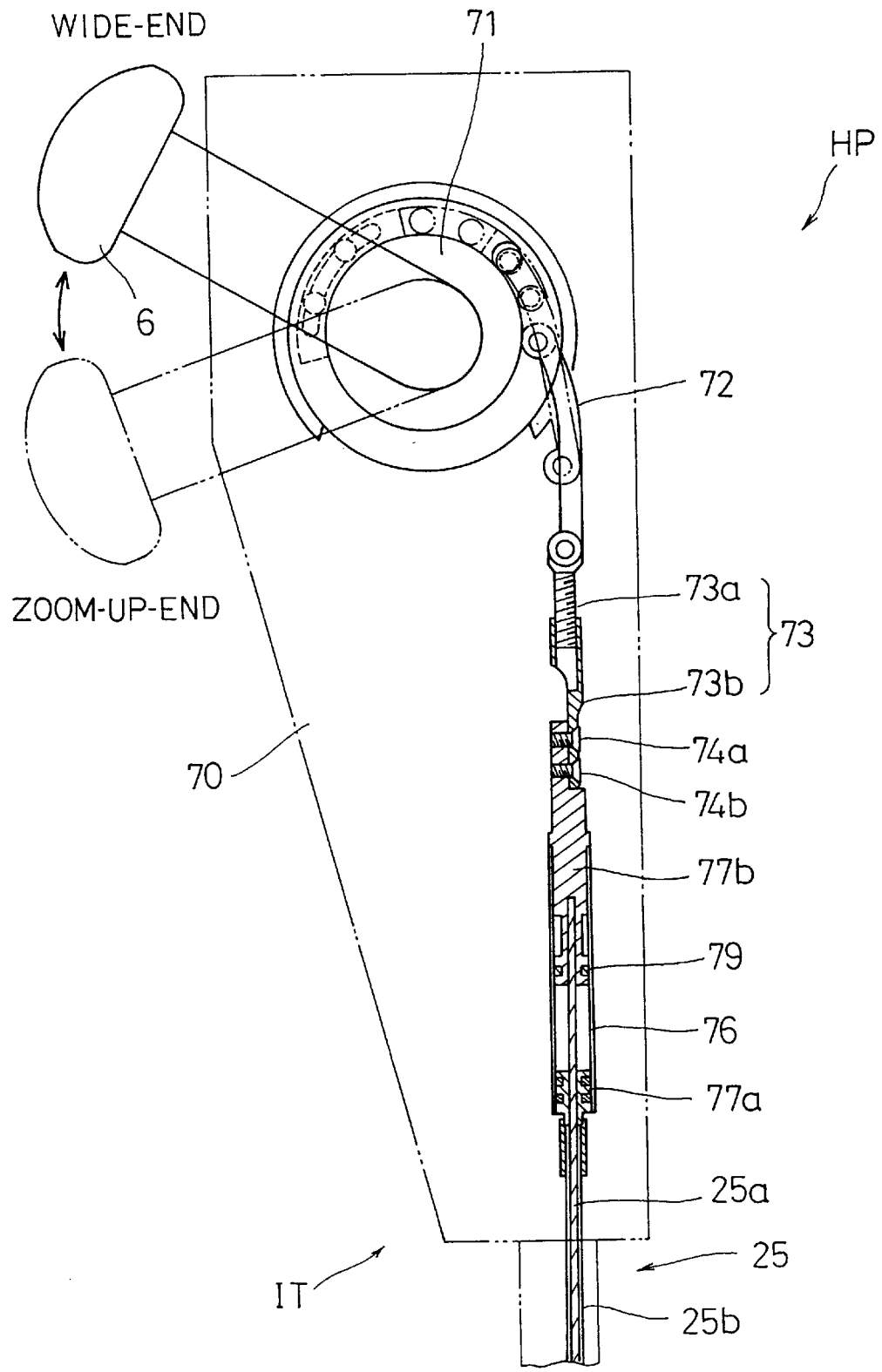
FIG. 15 shows a critical portion of the handpiece HP.

As described above, the proximal end of the imaging unit manipulation cable assembly 25 is operatively connected to the imaging unit manipulating lever 6 provided on the handpiece HP. This operative connection will be now described in detail with reference to FIG. 15, which shows a critical portion of the handpiece HP. The mechanism shown in FIG. 15 serves to convert the rotational movement of the lever 6 into the liner movement of the inner cable 25 of the manipulation cable assembly 25. The handpiece HP includes a frame 70 on which a drum 71 is pivotally mounted for rotation about its axis. The imaging unit manipulating lever 6 is fixedly connected to the drum 71. An elongated link 72 is provided which has a first end pivotally connected to the drum 71 at a peripheral portion of the drum 71 for rotation in a plane perpendicular to the axis of the drum 71.

A cylinder 76 is fixedly secured to the frame 70. The proximal end of the outer support tube 25b of the cable assembly 25 is secured to a first piston 77a which is fitted in the cylinder 76 at one end thereof and detachably secured to the frame 70 by means of a fixture (not shown). In this manner, the outer support tube 25b has its proximal end detachably secured to the handpiece HP. The first piston 77a is provided with two O-rings which serves to hermetically seal the gap between the cylinder 76 and the first piston 77a. The proximal end of the inner cable 25a of the cable assembly 25 is secured to a second piston 77b fitted in the cylinder 76 at the other end thereof. The second piston 77b is provided with an O-ring 79 fitted over the internal end thereof. The O-ring 79 serves to hermetically seal the gap between the cylinder 76 and the second piston 77b, as well as to provide a desirable friction against the axial movement of the second piston 77b relative to the cylinder 76. The second piston 77b has the external end extending out of the cylinder 76 and connected to a second end of the elongated link 72 through an adjustable link 73, which comprises a male screw member 73a and a female screw member 73b threadably engaging each other. The male screw member 73a is pivotally connected to the second end of the link 72 and the female screw member 73b is detachably secured to the second piston 77 by means of screws 74a and 74b.

In this manner, the inner cable 25a of the cable assembly 25 has its proximal end operatively connected to the manipulating lever 6, and the O-ring 79 serves to provide a desirable friction against the movement of the inner cable 25.

In operation, when the lever 6 is manipulated to rotate the drum 71, the second piston 77b is moved within the cylinder 76 in the axial direction, causing the inner cable 25a to displace relative to the outer support tube 25b of the cable assembly 25, with the result that the imaging unit IU is driven for macro-zooming operation.

The position of the inner cable 25a relative to the outer support tube 25b may be adjusted if necessary, by removing the screws 74a and 74b to disconnect the female screw member 74b from the second piston 77b, rotating the female screw member 74b to adjust the length of the adjustable link 73, and then reconnecting the female screw member 74b to the second piston 77b by means of the screws 74a and 74b.

It is noted that the distal end of the inner cable 25a is pulled by the axial slider 55 with the pull force which is mainly determined by the urging force applied to the axial slider 55 from the first compression helical spring 58 (FIGS. 5a and 5b). This pull force depends on the axial position of the axial slider 55 and will be at maximum when the axial slider 55 is at its rearmost position. The friction provided by the O-ring 79 is chosen to be large enough to prevent the movement of the inner cable 25a which could otherwise be produced by the pull force acting on the distal end of the inner cable 25a from the axial slider 55. In this manner, the imaging unit manipulating lever 6 may be retained at any selected position when the user leave the lever 6 free. Further, since the inside of the outer support tube 25b is completely separated from the outside at the proximal end by means of the cylinder 76 and the pistons 77a and 77b, no debris can enter the casing 27 of the imaging unit IT through the passage inside the outer support tube 25b.

Figure 16:
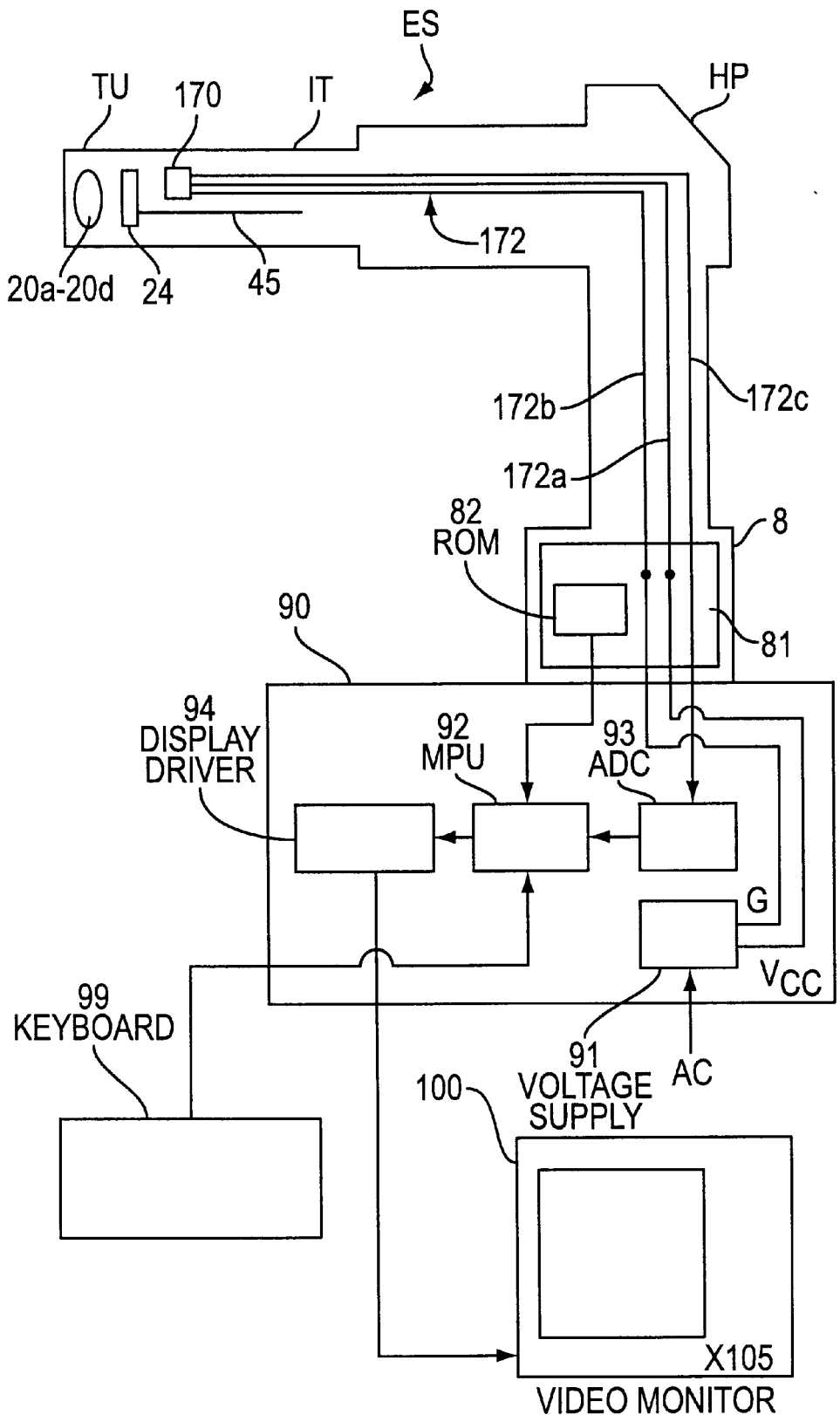
FIG. 16 is a schematic of the entirety of an electronic endoscope system.
Figure 17:
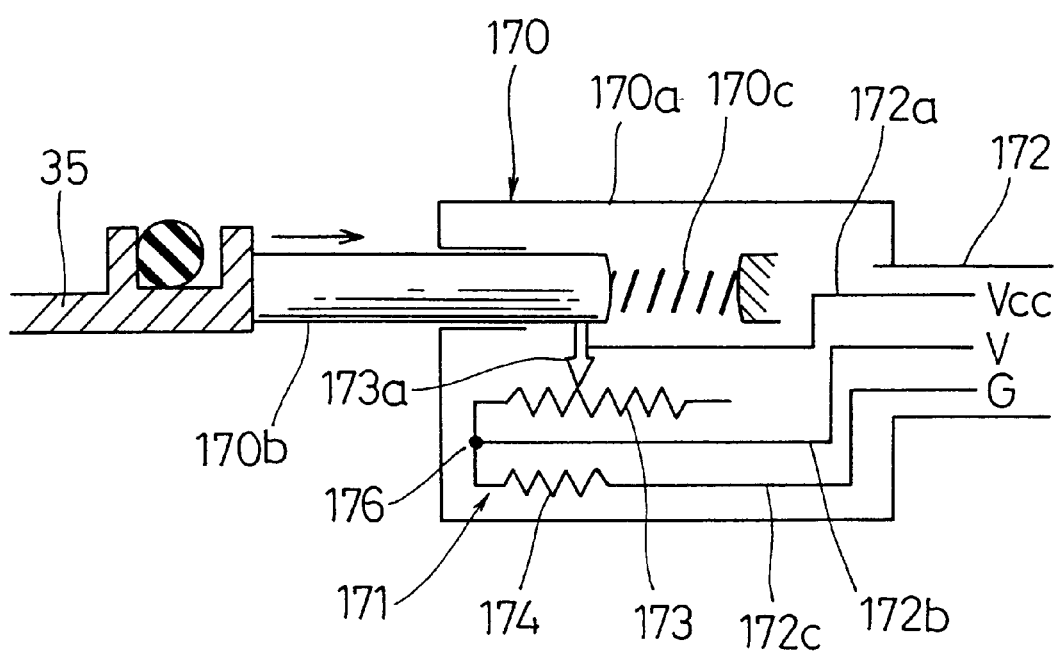
FIG. 17 is a schematic of a position sensor used in the system of FIG. 16.
Figure 18:
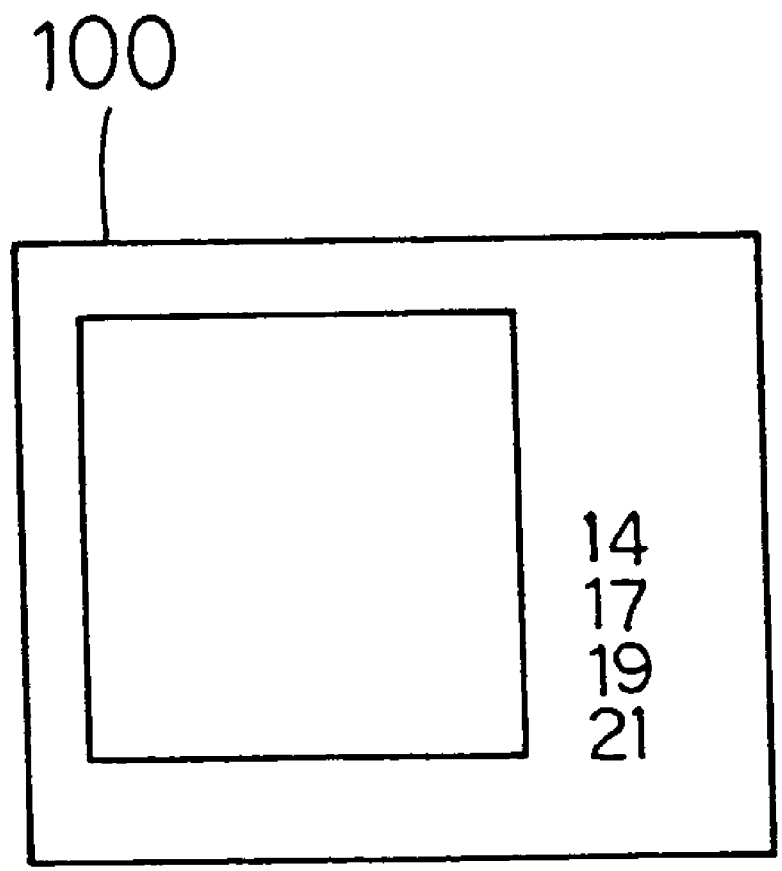
FIG. 18 is a schematic of a video monitor used in the system of FIG. 16.

Referring next to FIGS. 16 to 18 together with FIGS. 5a and 5b, an electronic endoscope system with a console will be described. FIG. 16 is a schematic of the entirety of an electronic endoscope system. FIGS. 17 and 18 are schematics of a position sensor and a video monitor, respectively, used in the system of FIG. 16.

In summary, the electronic endoscope system of FIG. 17 is specifically designed to provide indication of the display magnification ratio (DMR) of an endoscopic image. The term "display magnification ratio" means the ratio of the size of a displayed image of an object on the screen of a video monitor to the actual size of the object. By using this system, a user operating the endoscope can estimate the actual size of an object appearing on the screen, based on the size of the displayed image of the object and the indicated DMR value. The DMR value may be indicated on the same screen as the image of the object is displayed.

The system includes the endoscope ES and the console 90. As described above, the endoscope ES includes the handpiece HP with the manipulating lever 6, the tip unit TU with the housing 10, the insertion tube IT extending between and interconnecting the handpiece HP and the tip unit TU, the optical system disposed in the housing 10 for forming an endoscopic image of an object, the CCD 24 disposed in the housing 10 at a position at which an endoscopic image is formed by the optical system, and the electronics unit EU for transmitting video signals representing an endoscopic image taken by the CCD 24.

Also understood from the above, the endoscope ES further includes the mechanism for moving at least one of components of the optical system by manipulation of the manipulating lever 6 provided on the handpiece HP so as to achieve macro-zooming operation.

The endoscope ES further includes, specifically for use in the system of FIG. 16, a position sensor 170 disposed in the housing 10 of the tip unit TU for detecting axial position of one of axially movable components of the imaging unit IU (in the disclosed embodiment, the second carriage 35). The position sensor 170 is electrically connected to the console 90 through a cable 172 including three conductors 172a, 172b and 172c.

More particularly, as shown in FIGS. 5a and 5b, the position sensor 170 is secured to the inner surface of the inner cylinder 27a at the rear end thereof. The position sensor 170 comprises, as shown in FIG. 17, a sensor housing 170a adapted to be fixed to the inner cylinder 27a and a probe pin 170b supported by the sensor housing 170a for movement in the axial direction of the casing 27. The probe pin 170b is normally urged in the forward direction by a compression helical spring 70c, so that its front tip end of is urged against and kept in contact with the rear end surface of the second carriage 35. Accordingly, the prove pin 170b will be displaced in the axial direction along with the second carriage 35.

The position sensor 170 further comprises a potentiometer 171, which is schematically illustrated in FIG. 17. The potentiometer 171 comprises a variable resistor 173 and a fixed resistor 174 connected in series. The variable resistor 173 has a slider or wiper 173a mechanically connected to the probe pin 171 and electrically connected to the first conductor 172a of the cable 172, through which a supply voltage such as 5 volts is applied from the console 90. The node 176 between the resistors 173 and 174 is connected to the second conductor 172b of the cable 172, which in turn is connected to a ground voltage in the console 90. The terminal of the fixed resistor 174 opposite to the node 176 is connected to the third conductor 172c of the cable 172, which provides a detection voltage to the console 90. In this arrangement, the detection voltage occurring at the node 176 depends on the position of the wiper 173a and thus on the position of the second carriage 35 in the casing 27. Thus, the position of the second carriage 35 may be determined from the detection voltage.

With the position of the second carriage 35 thus determined, the position of the first carriage 34 and of the movable lenses 20b to 20d are also determined from the position of the second carriage 35, as the result that the current magnification ratio of the imaging unit IU depending on the current macro-zooming position can be determined. In the disclosed electronic endoscope system, the voltage obtained through the conductor 172c is directly converted to the value of the magnification ratio of the imaging unit IU.

The console 90 comprises a voltage supply 91, a microprocessor unit (MPU) 92 providing general control of the console 90, an analogue-to-digital convertor (ADC) 93 for digitizing the detection voltage and a display driver 94. Further, the console 90 is provided with a keyboard 99 and a video monitor 100 connected thereto.

The connector unit 8, which is detachably connected to the console 90 as described above, has a buffer circuit board 81 which is powered by the voltage supply 91 through the supply voltage conductor 172a and the ground conductor 172b. The connector unit 8 further comprises a read-only-memory (ROM) 82 mounted on the buffer circuit board 81, in which necessary information with respect to the characteristics of the endoscope ES is stored, including the specifications of the endoscope ES (for example, data indicating that the endoscope ES is an electronic endoscope having macro-zooming function) and a look-up table used for conversion of the digitized detection voltage into the corresponding value indicating the magnification ratio of the imaging unit IU. When the connector unit 8 is attached to the console 90, The information stored in the ROM 82 is read into the MPU 92 in the console 90.

The display magnification ratio depends on both the magnification ratio of the imaging unit IU and the size of the screen of the video monitor 100. The information about the size of the display screen may be entered by the user through the keyboard 99 into the MPU 92 or alternatively may be communicated from the video monitor 100 to the MPU 92 if the video display 100 is an intelligent video monitor.

In order to facilitate entering the information about the size of the display screen through the keyboard 99, the MPU 92 may provide a menu on the screen of the video monitor 100 which lists the possible sizes of the screen commonly used including, such as, fourteen, seventeen, nineteen and twenty-one inches as shown in FIG. 18. Then, it is only necessary for the user to select one of the listed screen sizes, as appropriate, through the keyboard 99.

The MPU 92 uses the value of the magnification ratio of the imaging unit IU read-in from the look-up table and the information about the screen size so as to determine the display magnification ratio, the value of which is transmitted to the display driver 94. The video signals received from the electronics unit EU, representing the image taken by the CCD 24, are also input to the display driver 94, which drives the video monitor 100 to display that image and the numerical indication of the display magnification ratio superimposed on the image, as shown in FIG. 16, in which the numerical indication shows "×105" meaning that the size of an observed object displayed on the screen is about one-hundred-and-five times the actual size of the object.

The numerical indication of the display magnification ratio may be selectively displayed on the display screen, so that this indication may be caused to disappear by the appropriate instruction entered from the keyboard 99.

In alternative arrangements, the position of any movable components other than the second carriage 35 may be detected by a suitable position sensor, which may be realized in any of various formes in addition to the disclosed position sensor 170 using the potentiometer 171.

While in the disclosed embodiment the present invention is utilized for the purpose of realizing macro-zooming function in an electronic endoscope, it is contemplated that the present invention may be also used to provide ordinary zooming function and/or focusing function alternatively or additionally to the macro-zooming function.

Further, in the disclosed embodiment, the support and guide mechanism for supporting and/or guiding the optical elements of the imaging unit IU comprises two movable carriages 34 and 35 for realizing macro-zooming function. Depending on the arrangement of the optical system actually adopted, however, the imaging unit may need only one movable carriage. It is contemplated that the present invention may be applied to an endoscope having such imaging unit, in which the second spring may be disposed between the only movable carriage and the casing or any other immovable component in the tip unit.

As clearly understood from the above, according to the present invention, the inner cable of the cable assembly is pulled through the manipulation of the manipulating lever, causing the axial slider to slide in the axial direction, which in turn drive the cam cylinder to rotate about the reference axis. This causes the axial displacement of any movable carriages in the imaging unit, so that focusing and/or zooming operations may be performed without any tilt of the movable carriage, resulting in a clear image observed.

Having described the present invention with reference to a preferred embodiment thereof, it is to be understood that the present invention is not limited to the disclosed embodiment, but may be embodied in various other forms without departing from the spirit and the scope of the present invention as defined by the appended claims.

What is claimed is:

1. An endoscope comprising:
a handpiece including a manipulating member mounted thereon;
a tip unit having front and rear ends and including i) a housing and ii) an imaging unit housed in said housing for obtaining an image as viewed in a view field in front of said tip unit, said housing having front and rear ends;
an insertion tube extending between and interconnecting said handpiece and said tip unit, said insertion tube having a proximal end connected to said handpiece and a distal end connected to said rear end of said housing of said tip unit;
a manipulation cable assembly received in said insertion tube and having a proximal end operatively connected to said manipulating member and a distal end operatively connected to said imaging unit so as to allow a user to manipulate said imaging unit through said manipulating member;
said imaging unit comprising i) a plurality of optical elements forming an optical system and ii) a support and guide mechanism for supporting and/or guiding said plurality of optical elements; and
said plurality of optical elements including i) a device having an image-bearing surface on which an image is to be formed and ii) a plurality of lenses arranged in line along a common optical axis for forming an image on said image-bearing surface of said device;
wherein said support and guide mechanism of said imaging unit comprises:
i) a first member fixedly mounted in said housing and including a hollow cylindrical portion having an axis and front and rear ends, said axis of said hollow cylindrical portion being a reference axis and defining an axial direction;
ii) a second member of a hollow cylindrical shape and having a cylindrical surface, said second member being fitted over said hollow cylindrical portion of said first member and being supported and guided for rotational movement about said reference axis with substantially no axial movement relative to said first member;

iii) a third member supported and guided for axial movement relative to said first and second members with substantially no rotational movement about said reference axis, said third member being operatively connected to said distal end of said manipulation cable assembly;

iv) at least one carriage carrying thereon one or more of said optical elements, said at least one carriage being supported and guided for axial movement relative to said first and second members with substantially no rotational movement about said reference axis;

v) a first cam mechanism provided between said second and third members for producing rotational movement of said second member in response to axial movement of said third member; and vi) a second cam mechanism provided between said second member and said at least one carriage for producing axial movement of said at least one carriage in response to rotational movement of said second member.

2. An endoscope according to claim 1, wherein:

said support and guide mechanism further comprises a first spring means for normally urging said third member in the axially forward direction.

3. An endoscope according to claim 1, wherein:

said first cam mechanism comprises i) a first cam slot formed in said second member and extending obliquely with respect to generators of said cylindrical surface of said second member and ii) a first pin provided on said third member and engaging said first cam slot.

4. An endoscope according to claim 3, wherein:

said first cam slot has front and rear end edges;

axially forward displacement of said third member is limited by the abutment of said first pin against said front end edge of said first cam slot; and axially rearward displacement of said third member is limited by the abutment of said first pin against said rear end edge of said first cam slot;

whereby axially foremost and rearmost positions of said third member are defined by the geometry of said first cam slot.

5. An endoscope according to claim 3, wherein:

said first cam slot is helical in shape and extends such that the angle formed between a generator of said cylindrical surface of said second member and said first cam slot falls in a range from 10 to 45 degrees.

6. An endoscope according to claim 1, wherein:

said first cam mechanism comprises i) a first cam slot formed in said second member and extending obliquely with respect to generators of said cylindrical surface of said second member and ii) a first pin provided on said third member and engaging said first cam slot; and said second cam mechanism comprises i) at least one second cam slot formed in said second member and extending obliquely with respect to generators of said cylindrical surface of said second member and ii) a second pin provided on each of said at least one carriage and engaging the associated one of said at least one second cam slot.

7. An endoscope according to claim 6, wherein:

said first cam slot has front and rear end edges and each of said at least one second cam slot has first and second end edges;

axially forward displacement of said third member is limited by the abutment of said first pin against said front end edge of said first cam slot, with a clearance remaining between said second pin and said first end edge of the associated one of said at least one second cam slot; and axially rearward displacement of said third member is limited by the abutment of said first pin against said rear end edge of said first cam slot, with a clearance remaining between said second pin and said second end edge of the associated one of said at least one second cam slot;

whereby axially foremost and rearmost positions of said third member are defined by the geometry of said first cam slot.

8. An endoscope according to claim 6, wherein:

said first cam slot is helical in shape and extends such that the angle formed between a generator of said cylindrical surface of said second member and said first cam slot falls in a range from 10 to 45 degrees.

9. An endoscope according to claim 6, wherein:

said support and guide mechanism further comprises a first spring means for normally urging said third member in the axially forward direction;

each of said at least one second cam slots has side edges; and said support and guide mechanism further comprises a second spring means for normally urging said at least one carriage in the axial direction so as to keep said second pin in contact with one of said side edges of the associated one of said at least one second cam slot.

10. An endoscope according to claim 9, wherein:

said first and second spring means provide respective urging forces which are chosen such that i) a torque normally acting on and tending to rotate said second member in one direction is produced from said urging force of said second spring means through said second cam mechanism, ii) an axial force normally acting on and tending to move said third member in the axially rearward direction is produced from said torque through said first cam mechanism and iii) said urging force of said first spring means is greater than said axial force.

11. An endoscope according to claim 6, wherein:

said second pin comprises i) a cylindrical head having an axis and a circumferential surface adapted for engagement with the associated one of said at least one second cam slots and ii) a threaded shank coaxial with said cylindrical head;

said cylindrical head further has an elongated recess formed therein at the top surface thereof and extending diametrically, for receiving therein the tip end of a screwdriver; and said elongated recess has both ends not reaching said circumferential surface of said cylindrical head, such that said cylindrical head has a complete circumferential surface with no cutout formed in that surface.

12. An endoscope according to claim 11, wherein:

said elongated recess has a semicircular cross-section as taken along a plane which contains said axis of said cylindrical head and extends in the longitudinal direction of said elongated recess.

13. An endoscope according to claim 1, wherein:

said plurality of lenses include at least one movable lens;

said at least one carriage includes a first carriage carrying thereon said at least one movable lens and a second carriage carrying thereon said device;

said first cam mechanism comprises i) a first cam slot formed in said second member and extending obliquely with respect to generators of said cylindrical surface of said second member and ii) a first pin provided on said third member and engaging said first cam slot; and said second cam mechanism comprises i) second and third cam slots formed in said second member and extending obliquely with respect to generators of said cylindrical surface of said second member in opposite directions and ii) second and third pins provided on said first and second carriages, respectively, and engaging said second and third cam slots, respectively.

14. An endoscope according to claim 13, wherein:

said first cam slot has front and rear end edges and each of said second and third cam slots has first and second end edges;

axially forward displacement of said third member is limited by the abutment of said first pin against said front end edge of said first cam slot, with a clearance remaining between said second pin and said first end edge of said second cam slot as well as a clearance remaining between said third pin and said first end edge of said third cam slot; and axially rearward displacement of said third member is limited by the abutment of said first pin against said rear end edge of said first cam slot, with a clearance remaining between said second pin and said second end edge of said second cam slot as well as a clearance remaining between said third pin and said second end edge of said third cam slot;

whereby axially foremost and rearmost positions of said third member are defined by the geometry of said first cam slot.

15. An endoscope according to claim 13, wherein:

said first cam slot is helical in shape and extends such that the angle formed between a generator of said cylindrical surface of said second member and said first cam slot falls in a range from 10 to 45 degrees.

16. An endoscope according to claim 13, wherein:

said support and guide mechanism further comprises a first spring means for normally urging said third member in the axially forward direction;

each of said second and third cam slots has side edges; and said support and guide mechanism further comprises a second spring means for normally urging said first and second carriages in the axially opposite directions apart from each other so as to keep said second and third pins in contact with one of said side edges of said second cam slot and one of said side edges of said third cam slot, respectively.

17. An endoscope according to claim 16, wherein:

said first and second spring means provide respective urging forces which are chosen such that i) a torque normally acting on and tending to rotate said second member in one direction is produced from said urging force of said second spring means through said second cam mechanism, ii) an axial force normally acting on and tending to move said third member in the axially rearward direction is produced from said torque through said first cam mechanism and iii) said urging force of said first spring means is greater than said axial force.

18. An endoscope according to claim 13, wherein:

each of said second and third pins comprises i) a cylindrical head having an axis and a circumferential surface adapted for engagement with the associated one of said second and third cam slots and ii) a threaded shank coaxial with said cylindrical head;

said cylindrical head further has an elongated recess formed therein at the top surface thereof and extending diametrically, for receiving therein the tip end of a screwdriver; and said elongated recess has both ends not reaching said circumferential surface of said cylindrical head, such that said cylindrical head has a complete circumferential surface with no cutout formed in that surface.

19. An endoscope according to claim 18, wherein:

said elongated recess has a semicircular cross-section as taken along a plane which contains said axis of said cylindrical head and extends in the longitudinal direction of said elongated recess.

20. An endoscope according to claim 1, wherein:

said manipulation cable assembly comprises an inner cable and an outer support tube, said inner cable being received in said outer support tube for sliding movement in the longitudinal direction relative to said outer support tube;

said outer support tube has a proximal end secured to said handpiece and a distal end secured to said imaging unit and said inner cable has a proximal end operatively connected to said manipulating member and a distal end connected to said third member, such that said third member may be pulled by said inner cable in the axially rearward direction when said manipulating member is manipulated for that purpose; and said handpiece is provided with friction means for providing a friction against the movement of said inner cable, said friction being large enough to prevent the movement of said inner cable which could otherwise be produced by a pull force acting on said distal end of said inner cable from said third member.

21. An endoscope according to claim 1, wherein:

said plurality of lenses include at least one movable lens;

said at least one carriage includes a first carriage carrying thereon said at least one movable lens; and said first carriage includes fine-adjustment means for providing fine adjustment for axial position of said at least one movable lens relative to said first carriage.

22. An endoscope according to claim 21, wherein:

said at least one carriage includes a second carriage carrying thereon said device;

said support and guide mechanism provides axial movements of said first and second carriages with a predetermined relationship established between them so as to provide macro-zooming function, for which each of said first and second carriages are moved between wide-end and zoom-up-end positions; and said fine-adjustment means is capable of providing said fine adjustment when said first and second carriages are in their zoom-up-end positions.

23. An endoscope according to claim 21, wherein:

said fine-adjustment means comprises i) a lens holder fixedly holding said at least one movable lens and mounted on said first carriage for axial displacement and ii) a set screw for securing said lens holder to said first carriage, such that said fine adjustment may be performed by loosening said set screw, displacing axially said lens holder relative to said first carriage, and then tightening again said set screw.

24. An endoscope according to claim 23, wherein:

said first carriage has i) an axial bore for receiving therein said lens holder and ii) an adjustment-tool-access hole for allowing access to said lens holder in said axial bore by a bar-like adjustment tool.

25. An endoscope according to claim 24, wherein:

said first and second members each has a screwdriver-access hole and an adjustment-tool-access hole which may be aligned, respectively, to said set screw and to said adjustment-tool-access hole formed in said first carriage.

26. An endoscope according to claim 23, wherein:

said lens holder has an outer circumferential surface and an annular groove formed in said outer circumferential surface for engaging a tip end of a bar-like adjustment tool for said fine adjustment.

27. An endoscope according to claim 1, wherein:

said device comprises a charge coupled device (CCD);

said imaging unit further comprises an electronics unit including a circuit board on which said CCD and circuitries associated with said CCD are mounted;

said at least one carriage includes an electronics unit carriage for carrying thereon said electronics unit; and said manipulation cable assembly and said electronics unit are electrically insulated from each other.

28. An endoscope according to claim 27, wherein:

said circuit board is rolled into a cylindrical roll; and said electronics unit includes an insulation layer made of a length of elongated electrically-insulative tape wrapped around said roll to provide electric insulation between said circuit board and said electronics unit carriage.

29. An endoscope according to claim 27, wherein:

said electronics unit carriage is made of an electrically-insulative material to provide electric insulation between said electronics unit and said manipulation cable assembly.

30. An endoscope according to claim 1, wherein:

said manipulation cable assembly comprises an inner cable and an outer support tube, said inner cable being received in said outer support tube for sliding movement in the longitudinal direction relative to said outer support tube;

said outer support tube comprises a coiled steel wire tube formed by closely coiling a length of steel wire, with elastic and adhesive curable-sealant being applied to the outside of said coiled steel wire tube between adjacent coils.

31. An endoscope according to claim 30, wherein:

said steel wire is a round steel wire having a circular cross-section; and the amount of said curable-sealant applied is selected such that when said coiled steel wire tube is not bent or curved, the surface of said sealant is recessed from the imaginary cylindrical surface defined by the outer diameter of said coiled steel wire tube.

32. An endoscope according to claim 30, wherein:

said curable-sealant is a silicone-rubber sealant.

33. An endoscope according to claim 30, wherein:

said insertion tube has an front end portion thereof adjacent to said tip unit constructed as a steerable portion; and a portion of said coiled steel wire tube that is housed in said steerable portion of said insertion tube has no sealant applied thereto but instead a flexible cover tube fitted thereover.

34. An endoscope according to claim 1, wherein:

said imaging unit further comprises a position sensor provided in said tip unit for detecting axial position of one of axially movable components of said imaging unit and providing an output signal representing a detected axial position; and said position sensor is connected with a console including i) a video monitor with a screen and ii) means for receiving said output signal from said position sensor so as to determine and display a display magnification ratio on said screen.

35. An endoscope according to claim 34, wherein:

said means for determination and display includes means for determining a display magnification ratio based on the size of said screen.

36. An endoscope according to claim 34, wherein:

said means for determination and display includes means for selectively preventing display of a display magnification ratio.

37. An endoscope according to claim 34, wherein:

said device comprises a charge coupled device (CCD);

said at least one carriage includes a CCD carriage for carrying thereon said CCD;

said position sensor is disposed to detect axial position of said CCD carriage.

38. An endoscope according to claim 1, wherein:

said support and guide mechanism is configured to provide for the axial movement of said at least one carriage so that said at least one carriage may perform a zooming operation.

39. An endoscope according to claim 1, wherein:

said support and guide mechanism is configured to provide for the axial movement of said at least one carriage so that said at least one carriage may perform a macro-zooming operation.

40. An endoscope according to claim 1, wherein:

said support and guide mechanism is configured to provide for the axial movement of said at least one carriage so that said at least one carriage may perform a focusing operation.

41. An imaging unit for an endoscope, comprising:

an axial slider disposed in a housing for sliding movement in the axial direction, said housing being connected to an distal end of an insertion tube of an endoscope;

a cable for manipulation of said axial slider, said cable having a distal end connected to said axial slider;

a fixed cylinder fixedly disposed in said housing;

two carriages including a first carriage carrying at least one lens and a second carriage carrying an image-sensing element of image transmitting means, at least one of said two carriages being received in said fixed cylinder for sliding movement in the axial direction; and a cam cylinder fitted over said fixed cylinder for rotation about an axis, said cam cylinder being adapted to be driven to rotate about said axis in response to the sliding movement of said axial slider, so as to drive said at least one of said two carriages that is received in said fixed cylinder for sliding movement to move in the axial direction.

42. An imaging unit for an endoscope according to claim 41, wherein:
said at least one of said two carriages that is received in said fixed cylinder for sliding movement is provided with a pin projecting toward said cam cylinder;
said axial slider is provided with a pin projecting toward said cam cylinder; and
said cam cylinder has a plurality of cam slots formed therein for engaging said pins, respectively.

43. An imaging unit for an endoscope, comprising:
an axial slider disposed in a housing for sliding movement in the axial direction, said housing being connected to an distal end of an insertion tube of an endoscope;
a cable for manipulation of said axial slider, said cable having a distal end connected to said axial slider;
a fixed cylinder fixedly disposed in said housing;
two carriages including a first carriage carrying at least one lens and a second carriage carrying an image-sensing element of image transmitting means, at least one of said two carriages being received in said fixed cylinder for sliding movement in the axial direction;
a cam cylinder fitted over said fixed cylinder for rotation about an axis, said cam cylinder being adapted to be driven to rotate about said axis in response to the sliding movement of said axial slider, so as to drive said at least one of said two carriages that is received in said fixed cylinder for sliding movement to move in the axial direction;
a first spring means for normally urging, in the axial direction, said at least one of said two carriages that is received in said fixed cylinder for sliding movement; and
a second spring means for normally urging, in the axially forward direction, said axial slider with an urging force greater than an urging of said first spring means.

44. An imaging unit for an endoscope according to claim 43, wherein:
said at least one of said two carriages that is received in said fixed cylinder for sliding movement is provided with a pin projecting toward said cam cylinder;
said axial slider is provided with a pin projecting toward said cam cylinder; and
said cam cylinder has a plurality of cam slots formed therein for engaging said pins, respectively.

45. An imaging unit for an endoscope, comprising:
an axial slider disposed in a housing for sliding movement in the axial direction, said housing being connected to an distal end of an insertion tube of an endoscope, said axial slider having a pin;
a cable for manipulation of said axial slider, said cable having a distal end connected to said axial slider;
a cam cylinder disposed for rotation about an axis and having an input cam slot formed therein, said input cam slot engaging said pin of said axial slider and having end edges; and
two carriages including a first carriage carrying at least one lens and a second carriage carrying an image-sensing element of image transmitting means;
wherein movement of said axial slider in the axial direction caused by said cable produces rotational movement of said cam cylinder, which in turn produces axial movement of at least one of said two carriages;
wherein the rotation range of said cam cylinder is limited by abutment between i) said pin moving along said input cam slot and ii) said end edges of said input cam slot.

46. An imaging unit for an endoscope according to claim 45, wherein:
at least one of said two carriages is disposed for sliding movement in the axial direction and has a pin projecting toward said cam cylinder;
said cam cylinder has an output cam slot formed therein, said output cam slot having end edges; and
said output cam slot is sufficiently long such that said pin of said at least one of said two carriages may avoid abutment with either of said end edges of said output cam slot even when said cam cylinder has been rotated to reach either limit of said rotation range.

47. An imaging unit for an endoscope, comprising:
an axial slider disposed in a housing for sliding movement in the axial direction, said housing being connected to an distal end of an insertion tube of an endoscope, said axial slider having a pin;
a cable for manipulation of said axial slider, said cable having a distal end connected to said axial slider;
a cam cylinder disposed for rotation about an axis and having an input cam slot formed therein, said input cam slot engaging said pin of said axial slider; and
two carriages including a first carriage carrying at least one lens and a second carriage carrying an image-sensing element of image transmitting means;
wherein movement of said axial slider in the axial direction caused by said cable produces rotational movement of said cam cylinder, which in turn produces axial movement of at least one of said two carriages;
wherein said input cam slot is so formed as to extend obliquely with respect to said axial direction at an angle falling in a range of 10 to 45 degrees.

48. An imaging unit for an endoscope according to claim 47, wherein:
said at least one of said two carriages that is disposed for axial movement is provided with a pin projecting toward said cam cylinder;
said axial slider is provided with a pin projecting toward said cam cylinder; and
said cam cylinder has a plurality of cam slots formed therein for engaging said pins, respectively.

49. An imaging unit for an endoscope, comprising:
at least one lens housed in a housing, said housing being connected to an distal end of an insertion tube of an endoscope;
image transmitting means for sensing an image formed by said at least one lens and transmitting said image, said image transmitting means including an image-sensing element;
means for causing movements of said at least one lens and said image-sensing element in the direction of the optical axis through manipulation of a manipulating member provided on a handpiece; and
means for providing fine adjustment of the position of said at least one lens within said housing in the direction of the optical axis when assembling.

50. An imaging unit for an endoscope, comprising:
at least one lens housed in a housing, said housing being connected to an distal end of an insertion tube of an endoscope;
image transmitting means for sensing an image formed by said at least one lens and transmitting said image, said image transmitting means including an image-sensing element; and a cable assembly received in said insertion tube, for displacing said at least one lens and/or said image-sensing element in the axial direction, said cable assembly including an outer support tube and an inner cable received in said outer support tube;

wherein said outer support tube comprises a coiled steel wire tube formed by closely coiling a length of steel wire with highly elastic curable-sealant applied to the outside of said coiled steel wire tube between adjacent coils thereof.

51. An imaging unit for an endoscope according to claim 50, wherein:

said steel wire has a circular cross-section; and the amount of said sealant applied is selected such that when said coiled steel wire tube is not curved, the surface of said sealant is recessed from the imaginary cylindrical surface defined by the outer diameter of said coiled steel wire tube.

52. An electronic endoscope comprising:

an insertion tube;

a housing connected to an distal end of said insertion tube;

at least one lens housed in said housing;

a charge coupled device (CCD) for sensing an image formed by said at least one lens, said CCD being housed in an electronics unit;

a cable assembly received in said insertion tube, for displacing said at least one lens and/or said CCD;

a first insulative layer formed from a length of thin, elongated electrically-insulative tape wrapped around the outer surface of said electronics unit;

a shield member of a hollow cylindrical shape fitted over said first insulative layer;

a second insulative layer formed from a length of thin, elongated electrically-insulative tape wrapped around the outer surface of said shield member; and a third insulative layer of resin material formed between said first and second layer and adjacent a portion of said shield member;

wherein said first, second and third layers provide electric insulation between said electronics unit and said cable assembly.

53. An electronic endoscope system comprising:

an endoscope including a handpiece with a manipulating member, a tip unit with a housing, an insertion tube extending between and interconnecting said handpiece and said tip unit, an optical system disposed in said housing for forming an endoscopic image of an object, a charge coupled device (CCD) disposed in said housing at a position at which an endoscopic image is formed by said optical system and a transmitter for transmitting video signals representing an endoscopic image taken by said CCD;

a console including a video monitor and a driver for driving said video monitor so as to display an endoscopic image on said video monitor;

said endoscope further including a system for moving at least one component of said optical system by manipulation of said manipulating member on said handpiece so as to achieve zooming operation;

said endoscope further including a position sensor for detecting a position of a movable component of said optical system in said housing and producing an output signal representing the detected position; and said console further including a display-magnification-ratio display for receiving said output signal from said position sensor, for converting said received output signal into a value indicating the display-magnification-ratio of an endoscopic image, and for displaying said value on said video monitor as a numerical indication of the display-magnification-ratio said display-magnification-ratio display includes a system for determining the display-magnification ratio based on the magnification ratio of said CCD and the screen size of said video monitor.

54. The electronic endoscope system according to claim 53, wherein:

said display-magnification-ratio display includes a system for selectively displaying said numerical indication of the display-magnification-ratio on said video monitor.

55. An electronic endoscope system comprising:

an endoscope including:
a handpiece with a manipulating member;
a tip unit with a housing;
an insertion tube extending between and interconnecting said handpiece and said tip unit;
an optical system disposed in said housing, for forming an endoscopic image of an object;
a movable carriage housed in and supported by said housing for axial displacement in said housing;
a charge coupled device (CCD) mounted on said movable carriage, for sensing an endoscopic image formed by said optical system; and
a device for transmitting video signals representing an endoscopic image taken by said CCD;

a console including a video monitor and a driver for driving said video monitor so as to display an endoscopic image on said video monitor;

said endoscope further including a system for displacing said movable carriage and at least one component of said optical system in an axial direction of said housing in response to manipulation of said manipulating member on said handpiece so as to achieve zooming operation;

said endoscope further including a position sensor for detecting a position of said movable carriage in said housing and producing an output signal representing the detected position; and said console further including a display-magnification-ratio-displaying system for receiving said output signal from said position sensor, for converting said received output signal into a value indicating the display-magnification-ratio of an endoscopic image, and for displaying said value on said video monitor as a numerical indication of the display-magnification-ratio said display-magnification-ratio display includes a system for determining the display-magnification-ratio based on the magnification ratio of said CCD and the screen size of said video monitor.

* * * * *